US010188693B2

(12) United States Patent
Wilson et al.

(10) Patent No.: US 10,188,693 B2
(45) Date of Patent: Jan. 29, 2019

(54) METHODS FOR TREATMENT OF ATHEROSCLEROSIS

(71) Applicant: Stealth BioTherapeutics Corp, Monaco (MC)

(72) Inventors: D. Travis Wilson, Newton, MA (US); Mark Bamberger, South Glastonbury, CT (US); Brian Blakey, Doylestown, PA (US); Marc W. Andersen, Raleigh, NC (US)

(73) Assignee: Stealth Biotherapeutics Corp, Monaco (MC)

( * ) Notice: Subject to any disclaimer, the term of this patent is extended or adjusted under 35 U.S.C. 154(b) by 0 days.

(21) Appl. No.: 14/418,827

(22) PCT Filed: Jul. 31, 2013

(86) PCT No.: PCT/US2013/053008
§ 371 (c)(1),
(2) Date: Jan. 30, 2015

(87) PCT Pub. No.: WO2014/022552
PCT Pub. Date: Feb. 6, 2014

(65) Prior Publication Data
US 2015/0157685 A1 Jun. 11, 2015

Related U.S. Application Data

(60) Provisional application No. 61/678,992, filed on Aug. 2, 2012, provisional application No. 61/695,807, filed on Aug. 31, 2012, provisional application No. 61/695,850, filed on Aug. 31, 2012.

(51) Int. Cl.
| | |
|---|---|
| A61K 31/22 | (2006.01) |
| A61K 31/40 | (2006.01) |
| A61K 38/08 | (2006.01) |
| A61K 45/06 | (2006.01) |
| A61K 38/07 | (2006.01) |
| A61K 31/366 | (2006.01) |
| A61K 31/404 | (2006.01) |
| A61K 31/505 | (2006.01) |
| A61K 31/215 | (2006.01) |
| A61K 31/351 | (2006.01) |
| A61P 9/10 | (2006.01) |

(52) U.S. Cl.
CPC ............ *A61K 38/07* (2013.01); *A61K 31/215* (2013.01); *A61K 31/22* (2013.01); *A61K 31/351* (2013.01); *A61K 31/366* (2013.01); *A61K 31/40* (2013.01); *A61K 31/404* (2013.01); *A61K 31/505* (2013.01); *A61K 45/06* (2013.01); *A61P 9/10* (2018.01)

(58) Field of Classification Search
CPC .. A61K 2300/00; A61K 31/22; A61K 31/366; A61K 31/40; A61K 31/404; A61K 31/505; A61K 31/215; A61K 31/351; A61K 38/08; A61K 45/06
USPC .................. 424/178.1, 179.1; 514/1.9, 21.9
See application file for complete search history.

(56) References Cited

U.S. PATENT DOCUMENTS

| | | | |
|---|---|---|---|
| 4,489,710 A | 12/1984 | Spitler | |
| 4,522,811 A | 6/1985 | Eppstein et al. | |
| 4,569,789 A | 2/1986 | Blattler et al. | |
| 4,625,014 A | 11/1986 | Senter et al. | |
| 4,638,045 A | 1/1987 | Kohn et al. | |
| 4,671,958 A | 6/1987 | Rodwell et al. | |
| 5,057,313 A | 10/1991 | Shih et al. | |
| 5,156,840 A | 10/1992 | Goers et al. | |
| 5,674,534 A | 10/1997 | Zale et al. | |
| 5,716,644 A | 2/1998 | Zale et al. | |
| 6,468,798 B1 | 10/2002 | Debs et al. | |
| 7,989,434 B2 | 8/2011 | Feng | |
| 8,039,273 B2 | 10/2011 | Jeffrey | |
| 8,697,657 B2* | 4/2014 | Wilson ................... | A61K 38/06 514/21.9 |
| 8,957,030 B2* | 2/2015 | Szeto ..................... | A61K 38/03 514/1.1 |
| 2007/0208073 A1 | 9/2007 | Bryson | |
| 2007/0264194 A1 | 11/2007 | Liu et al. | |
| 2009/0192095 A1* | 7/2009 | Franklin .......... | A61K 47/48038 514/1.1 |
| 2010/0086602 A1* | 4/2010 | Egashira .............. | A61K 9/0019 424/489 |
| 2011/0039766 A1 | 2/2011 | Szeto | |
| 2011/0182992 A1 | 7/2011 | Anantharamaiah et al. | |
| 2012/0035095 A1 | 2/2012 | Fogelman et al. | |
| 2013/0040901 A1* | 2/2013 | Szeto ..................... | A61K 38/06 514/21.9 |

FOREIGN PATENT DOCUMENTS

| | | |
|---|---|---|
| WO | WO-96/40073 | 12/1996 |
| WO | WO-99/15154 | 4/1999 |
| WO | WO-00/38651 | 7/2000 |
| WO | WO-2005/001023 | 1/2005 |
| WO | WO-2007/035640 A2 | 3/2007 |
| WO | WO-2011/025734 | 3/2011 |
| WO | WO-2011/106717 | 9/2011 |
| WO | WO-2011/116007 | 9/2011 |
| WO | WO-2012/088313 | 6/2012 |

OTHER PUBLICATIONS

Helsingin Yliopisto (Universit of Helsinki), "Mitochrondrial dysfunction is the root cause of many diseases," ScienceDaily.com (Year: 2017).*

(Continued)

*Primary Examiner* — Julie Ha
(74) *Attorney, Agent, or Firm* — Foley & Lardner LLP

(57) ABSTRACT

Disclosed herein are methods and compositions for preventing or treating atherosclerosis in a mammalian subject. The methods comprise administering to the subject an effective amount of an aromatic-cationic peptide and in some applications, a second active agent chemically linked to the peptide, to subjects in need thereof.

6 Claims, 18 Drawing Sheets

(56) References Cited

OTHER PUBLICATIONS

First Office Action and Search Report received for Chinese Patent Application No. 201380049785.5 dated Dec. 25, 2015, 16 pages with English translation.
First Office Action and Search Report received for Chinese Patent Application No. 201380049762.4 dated Mar. 4, 2016, 14 pages with English translation.
Chen, Min et al., "Mitochondria-targeted Peptide MTP-131 Alleviates Mitochondrial Dysfunction and Oxidative Damage in Human Trabecular Meshwork Cells," Invest. Ophthalmol. & Vis. Sci., (Sep. 2011), vol. 52, No. 10, pp. 7027-7037.
Chonn, Arcadio et al., "Recent Advances in Liposomal Drug-Delivery Systems," Current Opinion in Biotechnology, (1995), vol. 6, pp. 698-708.
Gregoriadis, G., "Engineering Liposomes for Drug Delivery: Progress and Problems," Trends in Biotechnology, (Dec. 1995), vol. 13, No. 12, pp. 527-537.
Hrab, Roman V. et al., "Prevention of fluvastatin-induced toxicity, mortality, and cardiac myopathy in pregnant rats by mevalonic acid supplementation," Teratology, (1994), vol. 50, No. 1, pp. 19-26, Abstract Only.
International Preliminary Report on Patentability received for Patent Application No. PCT/US2013/053007 dated Feb. 12, 2015, 9 pages.
International Preliminary Report on Patentability received in Patent Application No. PCT/US2013/053008 dated Feb. 12, 2015, 11 pages.
International Search Report and Written Opinion of the International Search Authority for Patent Application No. PCT/US2013/053007 dated Dec. 19, 2013, 12 pages.
International Search Report and Written Opinion of the International Search Authority received for Patent Application No. PCT/US2013/053008 dated Jan. 3, 2014, 14 pages.
Kozarich, John W. et al., "Next generation therapeutics: Looking to the horizon: Editorial overview," Current Opinion in Chemical Biology, (1998), vol. 2, Issue 4, pp. 439-440.
Lichtenberg, D. et al., "Liposomes: Preparation, Characterization and Preservation," Methods of Biochemical Analysis, (1988), vol. 33, pp. 337-462 (128 pages).
Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.
Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Szeto, Hazel H., "Cell-permeable, Mitochondrial-targeted, Peptide Antioxidants," The AAPS Journal, (2006), 8(2) Article 32, pp. E277-E283.
Weiner, Alan L., "Liposomes for Protein Delivery: Selecting Manufacture and Development Processes," Immunomethods, (1994), 4(3), pp. 201-209.
Zadelaar, Susanne et al., "Mouse Models for Atherosclerosis and Pharmaceutical Modifiers," Arterioscler Thromb Vasc Biol., (2007), vol. 27, No. 1, pp. 1706-1721.
Extended Search Report received for European Patent Application No. 13824883.6 dated Nov. 18, 2015, 8 pages.
Extended Search Report received for European Patent Application No. 13825389.3 dated Nov. 18, 2015, 12 pages.
Search Report issued on European Application 16174236.6, dated Jan. 13, 2017.
Japan Medical Journal, May 2006, No. 4282, pp. 65-69, English translation not available.
Japanese Journal of Medicine and Pharmaceutical Science, Mar. 2008, vol. 59, No. 3, pp. 357-380, English translation not available.
Office Action issued on Japanese Application 2015-525554, dated Apr. 10, 2017, English translation only.
Office Action issued on Japanese Application 2015-525555, dated Apr. 5, 2017, English translation only.
Prog. Med., Japan, Jan. 2004, vol. 24, No. 1, pp. 27-33, English translation not available.
The Journal of Practical Pharmacy, Nov. 2010, vol. 61, No. 12, pp. 3481-3485, English translation not available.
Third Office Action issued on Chinese Application 2013800497624, dated Oct. 9, 2017, English translation only.
Final Office Action on U.S. Appl. No. 14/418,809 dated Jun. 20, 2017.
Examination Report issued on European Application 13824883.6, dated Dec. 5, 2017.
Restriction Requirement issued on U.S. Appl. No. 14/418,809 dated Jan. 19, 2018.
Office Action issued on Chinese Application 201380049785.5, dated Jul. 17, 2017, English translation only.
Examination Report issued on Australian Application 2013296494, dated Apr. 3, 2018.
Extended Search Report issued on EP Application 17186931.6, dated Feb. 15, 2018.
Examination Report issued on Australian Application 2013296493, dated May 22, 2017.
Examination Report issued on Australian Application 2013296494, dated May 22, 2017.

\* cited by examiner

A.

B.

A.

B.

FIG. 4 (con't.)
C. Cholesterol Ester
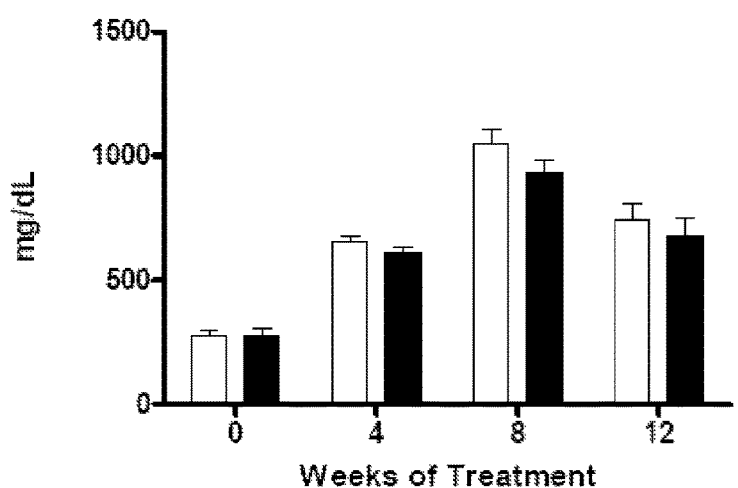
D. HDL-C
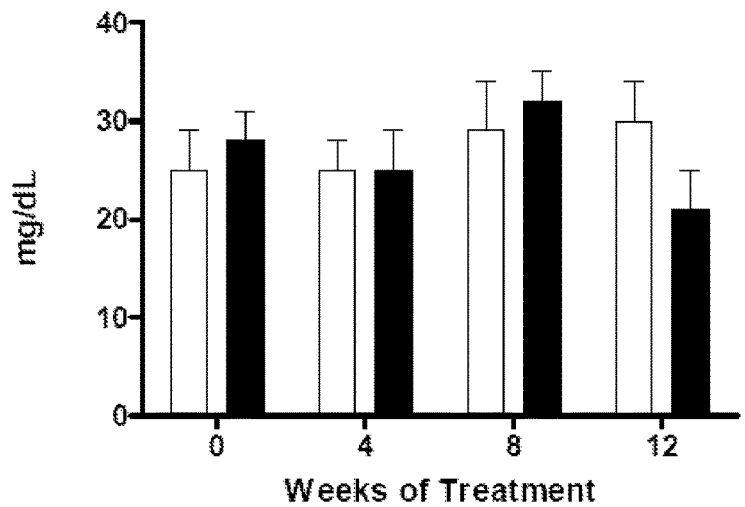

FIG. 4 (con't.)
E. VLDL-C
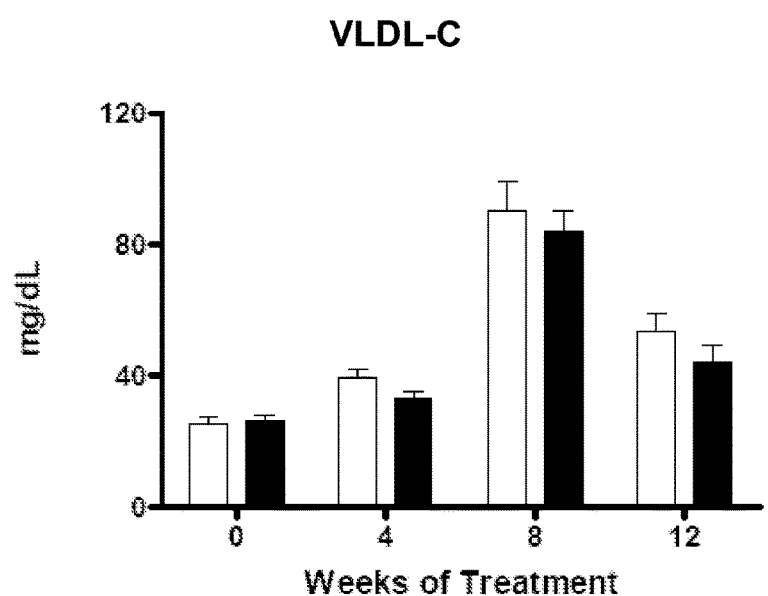
F. LDL-C
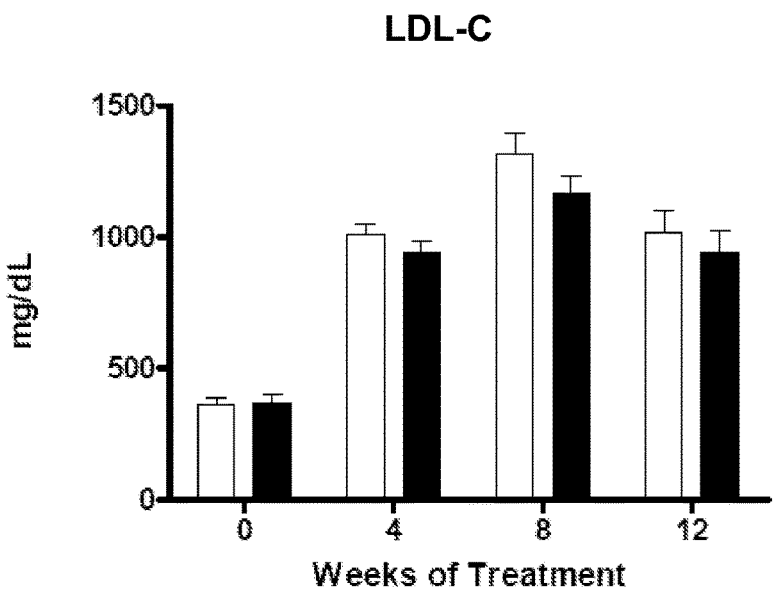

FIG. 4 (con't.)
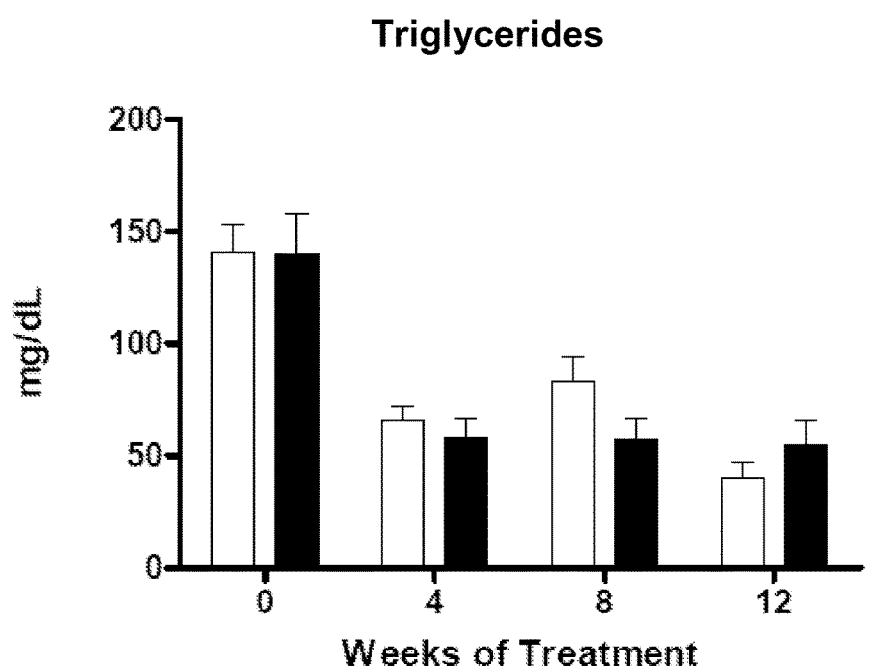

FIG. 4 (con't.)
H. Phospholipids
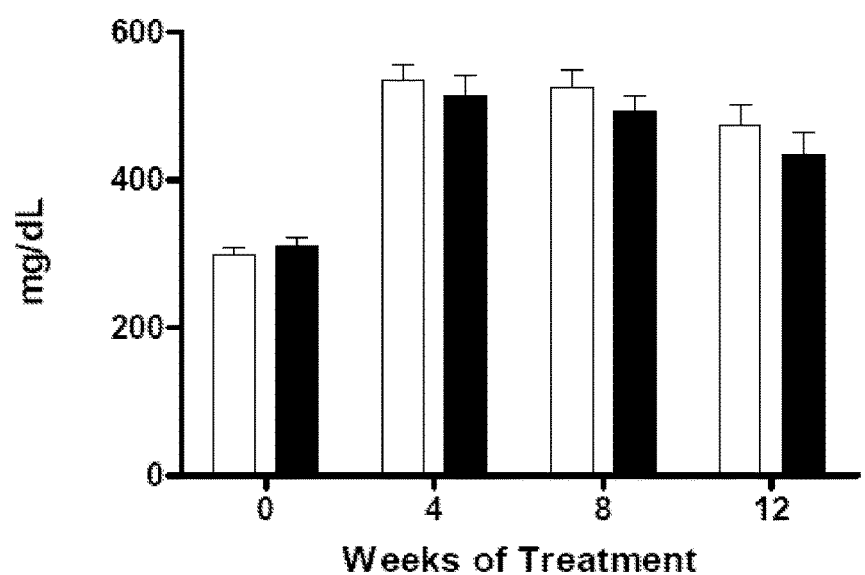
Weeks of Treatment

A.

B.

A.

B.

A.

Pro-drug          Statin   +   D-Arg-2'6'-Dmt-Lys-Phe-NH$_2$

B.

Pro-drug   Antihyperlipidemic drug  +  D-Arg-2'6'-Dmt-Lys-Phe-NH$_2$

Pro-drug        CRESTOR® or LIPITOR®     D-Arg-2'6'-Dmt-Lys-Phe-NH$_2$

Rosuvastatin (CRESTOR®)      Atorvastatin (LIPITOR®)

A =

*Indicates potential reactive sites to form pro-drug linkage

Formula I

Formula II

Formula III

A.

B.

FIG. 13 (con't.)
C.
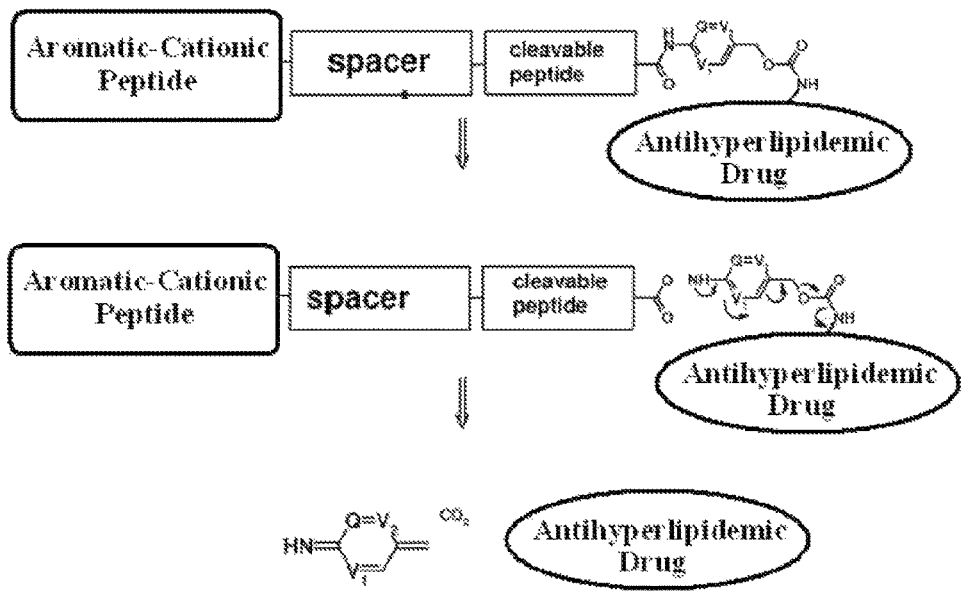
D.
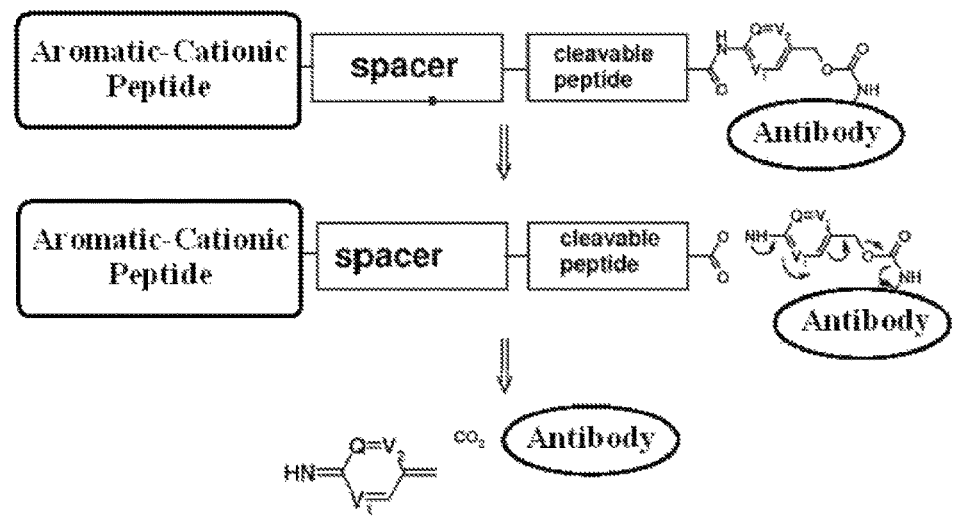

METHODS FOR TREATMENT OF ATHEROSCLEROSIS

CROSS-REFERENCE TO RELATED APPLICATIONS

This application is the U.S. 371 National Stage Application of International Application No.: PCT/US2013/053008, filed Jul. 31, 2013, which claims the benefit of and priority to U.S. Application No. 61/678,992 filed on Aug. 2, 2012, U.S. Application No. 61/695,807 filed on Aug. 31, 2012, and U.S. Application No. 61/695,850 filed on Aug. 31, 2012. The content of each application is incorporated herein by reference in its entirety.

TECHNICAL FIELD

The present technology relates generally to compositions and methods of preventing or treating atherosclerosis. In particular, embodiments of the present technology relate to administering aromatic-cationic peptides in effective amounts to prevent or treat atherosclerosis in mammalian subjects.

SUMMARY

The present technology relates to the treatment or prevention of atherosclerosis in mammals through the administration of a therapeutically effective amount of aromatic-cationic peptides and, in some embodiments, a second active agent. In some embodiments, the second active agent includes an antihyperlipidemic drug. In some embodiments, the second active agent includes a statin. In some embodiments, the second active agent and the aromatic-cationic peptide are chemically linked.

In one aspect, the present disclosure provides a pharmaceutical composition comprising (i) a peptide D-Arg-2'6'-Dmt-Lys-Phe-$NH_2$ or a pharmaceutically acceptable salt thereof, such as acetate or trifluoroacetate salt, and (ii) a second active agent, e.g., an antihyperlipidemic agent. In some embodiments, the second active agent comprises a statin. In some embodiments, the peptide and the second active agent are chemically linked.

In one aspect, the present disclosure provides a method for treating atherosclerosis in a mammalian subject, the method comprising administering an effective amount of peptide D-Arg-2'6'-Dmt-Lys-Phe-$NH_2$ or a pharmaceutically acceptable salt, such as acetate or trifluoroacetate salt.

In one aspect, the present disclosure provides a method for treating atherosclerosis in a mammalian subject, the method comprising administering an effective amount of (i) a peptide D-Arg-2'6'-Dmt-Lys-Phe-$NH_2$ or a pharmaceutically acceptable salt thereof and (ii) an antihyperlipidemic drug. In some embodiments, the peptide and the antihyperlipidemic drug are chemically linked. In some embodiments, the antihyperlipidemic drug includes one or more of: atorvastatin, simvastatin, pravastatin, fluvastatin, lovastatin, pitavastatin, rosuvastatin, clinofibrate, clofibrate, simfibrate, fenofibrate, bezafibrate, colestimide, colestyramine, ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and ZOCOR® (simvastatin). In some embodiments, the antihyperlipidemic drug is a statin. In some embodiments, the statin includes one or more of: ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and ZOCOR® (simvastatin).

In some embodiments, the peptide and the antihyperlipidemic agent are administered simultaneously. In some embodiments, the peptide and the antihyperlipidemic agent are administered sequentially in either order.

In one aspect, the present disclosure provides a method for preventing atherosclerosis in a mammalian subject, the method comprising administering a therapeutically effective amount of a peptide D-Arg-2'6'-Dmt-Lys-Phe-$NH_2$ or a pharmaceutically acceptable salt thereof.

In one aspect, the present disclosure provides a method for preventing atherosclerosis in a mammalian subject, the method comprising administering an effective amount of (i) a peptide D-Arg-2'6'-Dmt-Lys-Phe-$NH_2$ or a pharmaceutically acceptable salt thereof and (ii) an antihyperlipidemic drug. In some embodiments, the peptide and the antihyperlipidemic drug are chemically linked. In some embodiments, the antihyperlipidemic drug includes one or more of: atorvastatin, simvastatin, pravastatin, fluvastatin, lovastatin, pitavastatin, rosuvastatin, clinofibrate, clofibrate, simfibrate, fenofibrate, bezafibrate, colestimide, colestyramine, ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and ZOCOR® (simvastatin). In some embodiments, the antihyperlipidemic drug is a statin. In some embodiments, the statin includes one or more of: ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and ZOCOR® (simvastatin).

In some embodiments, the peptide and the antihyperlipidemic agent are administered simultaneously. In some embodiments, the peptide and the antihyperlipidemic agent are administered sequentially in either order. In some embodiments, the subject is predisposed to atherosclerosis.

In one aspect, the present disclosure provides a method for ameliorating the signs, symptoms or complications of atherosclerosis, the method comprising administering a therapeutically effective amount of a peptide D-Arg-2'6'-Dmt-Lys-Phe-$NH_2$ or a pharmaceutically acceptable salt thereof.

In one aspect, the present disclosure provides a method for ameliorating the signs, symptoms or complications of atherosclerosis, the method comprising administering an effective amount of (i) a peptide D-Arg-2'6'-Dmt-Lys-Phe-$NH_2$ or a pharmaceutically acceptable salt thereof and (ii) an antihyperlipidemic drug. In some embodiments, the antihyperlipidemic drug and the peptide are chemically linked. In some embodiments, the antihyperlipidemic drug includes one or more of: atorvastatin, simvastatin, pravastatin, fluvastatin, lovastatin, pitavastatin, rosuvastatin, clinofibrate, clofibrate, simfibrate, fenofibrate, bezafibrate, colestimide, colestyramine, ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and ZOCOR® (simvastatin). In some embodiments, the antihyperlipidemic drug is a statin. In some embodiments, the statin is includes one or more of: ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOl® (pravastatin), SIMCOR® (niacin extended-release/simvastatin), VYTORIN® (ezetimibe/simvastatin), and ZOCOR® (simvastatin).

In some embodiments, treatment of atherosclerosis includes decreasing the size or number of atherosclerotic plaques in the subject, and/or decreasing the cholesterol content of an atherosclerotic plaque in the subject.

In some embodiments, the peptide and the antihyperlipidemic agent are administered simultaneously. In some embodiments, the peptide and the antihyperlipidemic agent are administered sequentially in either order.

In some embodiments, the signs, symptoms or complications of atherosclerosis include one or more of: elevated levels total cholesterol, very low density lipoprotein cholesterol (VLDL-C), low density lipoprotein cholesterol (LDL-C), free (unesterified) cholesterol, cholesterol ester, phospholipids, triglycerides, and atherosclerotic lesions.

In one aspect, a method for delaying onset, ameliorating or eliminating statin side effects in a subject in need thereof is provided. In some embodiments, the method includes administering simultaneously, separately or sequentially with the statin, an effective amount of a peptide D-Arg-2'6'-Dmt-Lys-Phe-$NH_2$ or a pharmaceutically acceptable salt thereof. In some embodiments, the statin side effect includes one or more of myopathy, rhabdomyolysis, kidney failure, diabetes, memory loss, decreased coenzyme Q10 levels and mitochondrial dysfunction. In some embodiments, the statin includes one or more of atorvastatin, simvastatin, pravastatin, fluvastatin, lovastatin, pitavastatin, rosuvastatin, ADVICOR® (niacin extended-release/lovastatin), ALTOPREV® (lovastatin extended-release), CADUET® (amlodipine and atorvastatin), CRESTOR® (rosuvastatin), JUVISYNC® (sitagliptin/simvastatin), LESCOL® (fluvastatin), LESCOL XL (fluvastatin extended-release), LIPITOR® (atorvastatin), LIVALO® (pitavastatin), MEVACOR® (lovastatin), PRAVACHOL® (pravastatin), SIMCOR® (niacin extended-release/simvastatin), VYTORIN® (ezetimibe/simvastatin), and ZOCOR® (simvastatin).

In some aspects, a method for increasing statin dosage in a subject in need thereof is provided. In some embodiments, the method includes administering an effective amount of a statin at a first dosage level, and an aromatic-cationic peptide chemically linked to the statin; evaluating the subject for side-effects characteristic of the statin, wherein the side effects in the subject are reduced or absent as compared to a control subject administered the statin and not the aromatic-cationic peptide; administering a statin at a second dosage level, wherein the second dosage level is higher than the first statin dosage level. In some embodiments, the peptide is D-Arg-2'6'-Dmt-Lys-Phe-$NH_2$. In some embodiments, the statin includes LIPITOR® or CRESTOR®. In some embodiments, the side effect characteristic of the statin includes one or more of myopathy, rhabdomyolysis, kidney failure, diabetes, memory loss, decreased coenzyme Q10 levels and mitochondrial dysfunction.

In some embodiments, ameliorating the signs, symptoms or complications of atherosclerosis includes decreasing the size or number of atherosclerotic plaques in the subject, and/or decreasing the cholesterol content of an atherosclerotic plaque in the subject.

As noted above, in some embodiments of the present methods and compositions, the aromatic-cationic peptides of the present disclosure, such as D-Arg-2'6'-Dmt-Lys-Phe-$NH_2$ or a pharmaceutically acceptable salt thereof such as acetate or trifluoroacetate salt, and the antihyperlipidemic drug are chemically linked.

In some embodiments, the antihyperlipidemic drug is a statin. In some embodiments, the aromatic-cationic peptide and the statin are linked using a labile linkage that is hydrolyzed in vivo to release the peptide and the antihyperlipidemic drug. In some embodiments, the labile linkage comprises an ester linkage, a carbonate linkage, or a carbamate linkage.

In some embodiments of the methods and compositions disclosed herein, the antihyperlipidemic drug is an anti-PCSK9 antibody. In some embodiments, the aromatic-cationic peptide and the anti-PCSK9 antibody are linked using a bifunctional protein coupling agent. In some embodiments, the bifunctional protein coupling agent is N-succinimidyl-3-(2-pyridyldithio) propionate (SPDP), succinimidyl-4-(N-maleimidomethyl)cyclohexane-1-carboxylate (SMCC), iminothiolane (IT), a bifunctional derivative of an imidoester, an active ester, an aldehyde, a bis-azido compound, a bis-diazonium derivative, a diisocyanate, or a bis-active fluorine compound. In some embodiments, the aromatic-cationic peptide and the anti-PCSK9 antibody are linked using a labile linkage. In some embodiments, the labile linkage comprises an ester linkage, a carbonate linkage, or a carbamate linkage.

In some embodiments of the methods and compositions disclosed herein, the antihyperlipidemic agent is an Apo-B antisense oligonucleotide. In some embodiments, the aromatic-cationic peptide and the Apo-B antisense oligonucleotide are linked using a labile linkage. In some embodiments, the labile linkage comprises an ester linkage, a carbonate linkage, or a carbamate linkage.

In some embodiments, the peptides used in the compositions and methods disclosed herein is defined by formula I:

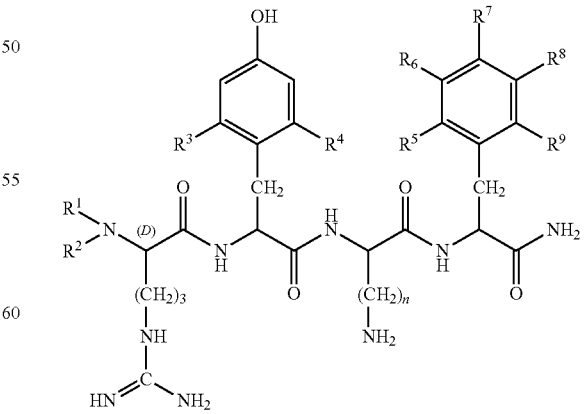

wherein $R^1$ and $R^2$ are each independently selected from
(i) hydrogen;
(ii) linear or branched $C_1$-$C_6$ alkyl;

(iii) 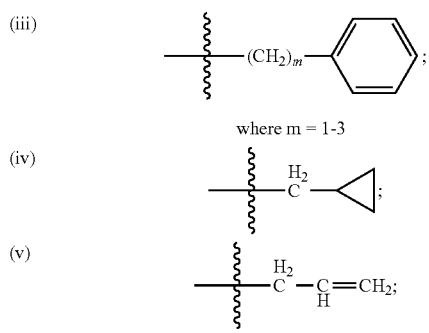

where m = 1-3

(iv)

(v)

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;

$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In some embodiments, $R^1$ and $R^2$ are hydrogen; $R^3$ and $R^4$ are methyl; $R^5$, $R^6$, $R^7$, $R^8$, and $R^9$ are all hydrogen; and n is 4.

In some embodiments, the peptides used in the methods and compositions disclosed herein are defined by formula II:

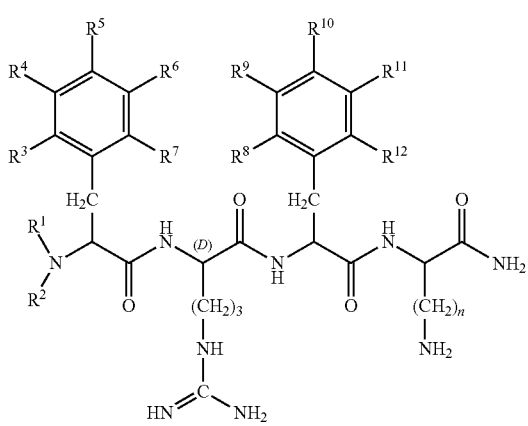

wherein $R^1$ and $R^2$ are each independently selected from
(i) hydrogen;
(ii) linear or branched $C_1$-$C_6$ alkyl;

(iii) 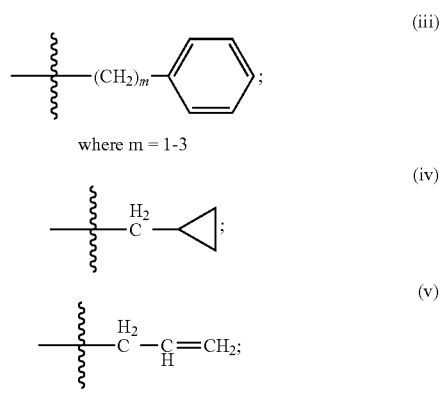

where m = 1-3

(iv)

(v)

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In some embodiments, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In some embodiments, the peptide comprises a tyrosine or a 2',6'-dimethyltyrosine (Dmt) residue at the N-terminus. For example, the peptide may have the formula Tyr-D-Arg-Phe-Lys-NH$_2$ or 2'6'-Dmt-D-Arg-Phe-Lys-NH$_2$. In another embodiment, the peptide comprises a phenylalanine or a 2'6'-dimethylphenylalanine residue at the N-terminus. For example, the peptide may have the formula Phe-D-Arg-Phe-Lys-NH$_2$ or 2'6'-Dmp-D-Arg-Phe-Lys-NH$_2$. In a particular embodiment, the aromatic-cationic peptide has the formula D-Arg-2'6'-Dmt-Lys-Phe-NH$_2$.

The aromatic-cationic peptides may be administered in a variety of ways. In some embodiments, the peptides may be administered orally, topically, intranasally, intraperitoneally, intravenously, subcutaneously, or transdermally (e.g., by iontophoresis).

DETAILED DESCRIPTION

Figure 1:
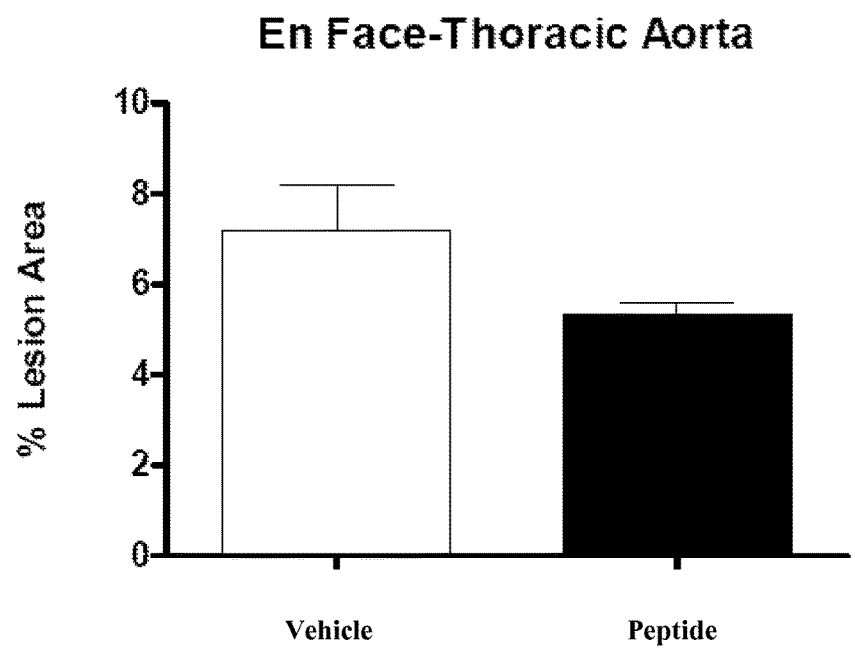
FIG. 1A is a graph showing the % lesion area in control mice (vehicle only—white bar) and test mice (aromatic-cationic peptide D-Arg-2'6'-Dmt-Lys-Phe-NH$_2$—dark bars) after 12 weeks of vehicle or peptide administration.
FIG. 1B is a photograph showing atherosclerotic lesions on aorta from a subject receiving vehicle only (left panel) or aromatic-cationic peptide (right panel).
Figure 1:
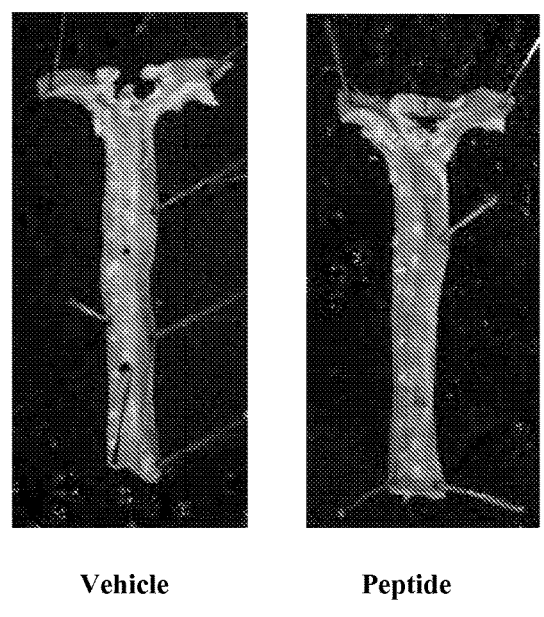

It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the prevention of, or a decrease in, atherosclerosis or one or more symptoms associated with atherosclerosis. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In the methods described herein, the aromatic-cationic peptides may be administered to a subject having one or more signs or symptoms of atherosclerosis. For example, a "therapeutically effective amount" of the aromatic-cationic peptides is meant levels in which the physiological effects of atherosclerosis are, at a minimum, ameliorated. In some embodiments, signs, symptoms or complications of atherosclerosis include, but are not limited to: increased plasma total cholesterol, increased plasma free cholesterol, increased plasma cholesterol ester, lesions (e.g. aortic lesions), increased plasma very low-density lipoprotein, increased plasma low density lipoprotein and/or increased plasma phospholipids.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the terms "treating" or "treatment" or "alleviation" refers to both therapeutic treatment and prophylactic or preventative measures, wherein the object is to prevent or slow down (lessen) the targeted pathologic condition or disorder. For example, a subject is successfully "treated" for atherosclerosis if, after receiving a therapeutic amount of the aromatic-cationic peptides according to the methods described herein, the subject shows observable and/or measurable reduction in or absence of one or more signs, symptoms or complications of atherosclerosis, such as, e.g., reduced total plasma cholesterol, free cholesterol, cholesterol ester, very low-density lipoprotein cholesterol (VLDL-C), low density lipoprotein cholesterol (LDL-C), phospholipids, lesion size and/or number (e.g. aortic lesions), lowered levels of cholesterol in the aortic tissue and/or aortic plaques, and/or lowered levels of cholesterol atherosclerotic lesions or plaques as compared to a subject not treated with the therapeutic aromatic-cationic peptide. It is also to be appreciated that the various modes of treatment or prevention of medical conditions as described are intended to mean "substantial," which includes total but also less than total treatment or prevention, and wherein some biologically or medically relevant result is achieved.

As used herein, "prevention" or "preventing" of a disorder or condition refers to one or more compounds that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing atherosclerosis includes reducing to, or maintaining at, normal levels one or more signs, symptoms or complications of atherosclerosis including, but not limited to total plasma cholesterol, free cholesterol, cholesterol ester, very low-density lipoprotein cholesterol, low density lipoprotein cholesterol, phospholipids, lesion size and/or number (e.g. aortic lesions), levels of cholesterol in the aortic tissue and/or aortic plaques, and/or levels of cholesterol atherosclerotic lesions or plaques as compared to a subject not treated with the therapeutic aromatic-cationic peptide.

As used herein, the terms "drug" and "agent" are synonymous.

As used herein the terms "antihyperlipidemic agent" or "antihyperlipidemic drug" are synonymous with the terms "hypolipidemic agent" or "hypolipidemic drug."

Methods of Prevention or Treatment

The present technology relates to the treatment or prevention of atherosclerosis by administration of aromatic-cationic peptides and, in some embodiments, aromatic-cationic peptides in conjunction with one or more active agents to a subject in need thereof. For example, the present technology relates to the treatment or prevention of atherosclerosis by administration of aromatic-cationic peptides, and in some embodiments, an aromatic-cationic peptide and one or more antihyperlipidemic drugs (e.g., statins) to a subject in need thereof. In some embodiments, the antihyperlipidemic drug and the aromatic-cationic peptide are chemically linked.

In one embodiment, the aromatic-cationic peptides and/or one or more agents are administered in dosages that are sub-therapeutic for each agent when administered separately. However, in some embodiments, the combination of the two agents results in synergism, which provides an enhanced effect that is not observed when each of the agents are administered individually at higher doses. In one embodiment, the administration of the aromatic-cationic peptide and one or more agents "primes" the tissue, so that it is more responsive to the therapeutic effects of the other agent. Thus, in some embodiments, a lower dose of the aromatic-cationic peptide and/or the one or more agents (e.g., antihyperlipidemic drugs, such as statins) can be administered, and yet, a therapeutic effect is still observed.

In some embodiments, the subject (e.g, a subject suffering from atherosclerosis, and/or exhibiting the signs, symptoms or complications of atherosclerosis, and/or who is predisposed to atherosclerosis or the signs, symptoms or complications of atherosclerosis) is administered the peptide, or is administered a peptide and one or more antihyperlipidemic drugs (e.g., statins) simultaneously, separately, or sequentially. In some embodiments, the subject is administered the peptide or is administered the peptide and one or more antihyperlipidemic drugs (e.g., statins), before atherosclerosis or before the signs, symptoms or complications of atherosclerosis are evident.

Aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. For example, the peptide may have no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid. Typically, a peptide has a positively charged N-terminal amino group and a negatively charged C-terminal carboxyl group. The charges cancel each other out at physiological pH.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal. In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

Aromatic-cationic peptides include, but are not limited to, the following peptide examples:

Lys-D-Arg-Tyr-NH$_2$

Phe-D-Arg-His

D-Tyr-Trp-Lys-NH$_2$

Trp-D-Lys-Tyr-Arg-NH$_2$

Tyr-His-D-Gly-Met

Phe-Arg-D-His-Asp

Tyr-D-Arg-Phe-Lys-Glu-NH$_2$

Met-Tyr-D-Lys-Phe-Arg

D-His-Glu-Lys-Tyr-D-Phe-Arg

Lys-D-Gln-Tyr-Arg-D-Phe-Trp-NH$_2$

Phe-D-Arg-Lys-Trp-Tyr-D-Arg-His

Gly-D-Phe-Lys-Tyr-His-D-Arg-Tyr-NH$_2$

Val-D-Lys-His-Tyr-D-Phe-Ser-Tyr-Arg-NH$_2$

Trp-Lys-Phe-D-Asp-Arg-Tyr-D-His-Lys

Lys-Trp-D-Tyr-Arg-Asn-Phe-Tyr-D-His-NH$_2$

Thr-Gly-Tyr-Arg-D-His-Phe-Trp-D-His-Lys

Asp-D-Trp-Lys-Tyr-D-His-Phe-Arg-D-Gly-Lys-NH$_2$

D-His-Lys-Tyr-D-Phe-Glu-D-Asp-D-His-D-Lys-Arg-Trp-NH$_2$

Ala-D-Phe-D-Arg-Tyr-Lys-D-Trp-His-D-Tyr-Gly-Phe

Tyr-D-His-Phe-D-Arg-Asp-Lys-D-Arg-His-Trp-D-His-Phe

Phe-Phe-D-Tyr-Arg-Glu-Asp-D-Lys-Arg-D-Arg-His-Phe-NH$_2$

Phe-Try-Lys-D-Arg-Trp-His-D-Lys-D-Lys-Glu-Arg-D-Tyr-Thr

Tyr-Asp-D-Lys-Tyr-Phe-D-Lys-D-Arg-Phe-Pro-D-Tyr-His-Lys

Glu-Arg-D-Lys-Tyr-D-Val-Phe-D-His-Trp-Arg-D-Gly-Tyr-Arg-D-Met-NH$_2$

Arg-D-Leu-D-Tyr-Phe-Lys-Glu-D-Lys-Arg-D-Trp-Lys-D-Phe-Tyr-D-Arg-Gly

D-Glu-Asp-Lys-D-Arg-D-His-Phe-Phe-D-Val-Tyr-Arg-Tyr-D-Tyr-Arg-His-Phe-NH$_2$

Asp-Arg-D-Phe-Cys-Phe-D-Arg-D-Lys-Tyr-Arg-D-Tyr-Trp-D-His-Tyr-D-Phe-Lys-Phe

His-Tyr-D-Arg-Trp-Lys-Phe-D-Asp-Ala-Arg-Cys-D-Tyr-His-Phe-D-Lys-Tyr-His-Ser-NH$_2$

Gly-Ala-Lys-Phe-D-Lys-Glu-Arg-Tyr-His-D-Arg-D-Arg-Asp-Tyr-Trp-D-His-Trp-His-D-Lys-Asp

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$

In one embodiment, the aromatic-cationic peptide has the formula Phe-D-Arg-Phe-Lys-NH$_2$. In another embodiment, the aromatic-cationic peptide has the formula D-Arg-2'6'-Dmt-Lys-Phe-NH$_2$.

The peptides mentioned herein and their derivatives can further include functional analogs. A peptide is considered a functional analog if the analog has the same function as the stated peptide. The analog may, for example, be a substitution variant of a peptide, wherein one or more amino acids are substituted by another amino acid. Suitable substitution variants of the peptides include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of peptides include, but are not limited to, the aromatic-cationic peptides shown in Table 5.

TABLE 5

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | $NH_2$ |
| Tyr | D-Arg | Phe | Orn | $NH_2$ |
| Tyr | D-Arg | Phe | Dab | $NH_2$ |
| Tyr | D-Arg | Phe | Dap | $NH_2$ |
| 2'6'Dmt | D-Arg | Phe | Lys | $NH_2$ |
| 2'6'Dmt | D-Arg | Phe | Lys-NH(CH$_2$)$_2$—NH-dns | $NH_2$ |
| 2'6'Dmt | D-Arg | Phe | Lys-NH(CH$_2$)$_2$—NH-atn | $NH_2$ |
| 2'6'Dmt | D-Arg | Phe | dnsLys | $NH_2$ |
| 2'6'Dmt | D-Cit | Phe | Lys | $NH_2$ |
| 2'6'Dmt | D-Cit | Phe | Ahp | $NH_2$ |
| 2'6'Dmt | D-Arg | Phe | Orn | $NH_2$ |
| 2'6'Dmt | D-Arg | Phe | Dab | $NH_2$ |
| 2'6'Dmt | D-Arg | Phe | Dap | $NH_2$ |
| 2'6'Dmt | D-Arg | Phe | Ahp(2-aminoheptanoic acid) | $NH_2$ |
| Bio-2'6'Dmt | D-Arg | Phe | Lys | $NH_2$ |
| 3'5'Dmt | D-Arg | Phe | Lys | $NH_2$ |
| 3'5'Dmt | D-Arg | Phe | Orn | $NH_2$ |
| 3'5'Dmt | D-Arg | Phe | Dab | $NH_2$ |
| 3'5'Dmt | D-Arg | Phe | Dap | $NH_2$ |
| Tyr | D-Arg | Tyr | Lys | $NH_2$ |
| Tyr | D-Arg | Tyr | Orn | $NH_2$ |
| Tyr | D-Arg | Tyr | Dab | $NH_2$ |
| Tyr | D-Arg | Tyr | Dap | $NH_2$ |
| 2'6'Dmt | D-Arg | Tyr | Lys | $NH_2$ |
| 2'6'Dmt | D-Arg | Tyr | Orn | $NH_2$ |
| 2'6'Dmt | D-Arg | Tyr | Dab | $NH_2$ |
| 2'6'Dmt | D-Arg | Tyr | Dap | $NH_2$ |
| 2'6'Dmt | D-Arg | 2'6'Dmt | Lys | $NH_2$ |
| 2'6'Dmt | D-Arg | 2'6'Dmt | Orn | $NH_2$ |
| 2'6'Dmt | D-Arg | 2'6'Dmt | Dab | $NH_2$ |
| 2'6'Dmt | D-Arg | 2'6'Dmt | Dap | $NH_2$ |
| 3'5'Dmt | D-Arg | 3'5'Dmt | Arg | $NH_2$ |
| 3'5'Dmt | D-Arg | 3'5'Dmt | Lys | $NH_2$ |
| 3'5'Dmt | D-Arg | 3'5'Dmt | Orn | $NH_2$ |
| 3'5'Dmt | D-Arg | 3'5'Dmt | Dab | $NH_2$ |
| Tyr | D-Lys | Phe | Dap | $NH_2$ |
| Tyr | D-Lys | Phe | Arg | $NH_2$ |
| Tyr | D-Lys | Phe | Lys | $NH_2$ |
| Tyr | D-Lys | Phe | Orn | $NH_2$ |
| 2'6'Dmt | D-Lys | Phe | Dab | $NH_2$ |
| 2'6'Dmt | D-Lys | Phe | Dap | $NH_2$ |
| 2'6'Dmt | D-Lys | Phe | Arg | $NH_2$ |
| 2'6'Dmt | D-Lys | Phe | Lys | $NH_2$ |
| 3'5'Dmt | D-Lys | Phe | Orn | $NH_2$ |
| 3'5'Dmt | D-Lys | Phe | Dab | $NH_2$ |
| 3'5'Dmt | D-Lys | Phe | Dap | $NH_2$ |
| 3'5'Dmt | D-Lys | Phe | Arg | $NH_2$ |
| Tyr | D-Lys | Tyr | Lys | $NH_2$ |
| Tyr | D-Lys | Tyr | Orn | $NH_2$ |
| Tyr | D-Lys | Tyr | Dab | $NH_2$ |
| Tyr | D-Lys | Tyr | Dap | $NH_2$ |
| 2'6'Dmt | D-Lys | Tyr | Lys | $NH_2$ |
| 2'6'Dmt | D-Lys | Tyr | Orn | $NH_2$ |
| 2'6'Dmt | D-Lys | Tyr | Dab | $NH_2$ |
| 2'6'Dmt | D-Lys | Tyr | Dap | $NH_2$ |
| 2'6'Dmt | D-Lys | 2'6'Dmt | Lys | $NH_2$ |
| 2'6'Dmt | D-Lys | 2'6'Dmt | Orn | $NH_2$ |
| 2'6'Dmt | D-Lys | 2'6'Dmt | Dab | $NH_2$ |
| 2'6'Dmt | D-Lys | 2'6'Dmt | Dap | $NH_2$ |
| 2'6'Dmt | D-Arg | Phe | dnsDap | $NH_2$ |
| 2'6'Dmt | D-Arg | Phe | atnDap | $NH_2$ |
| 3'5'Dmt | D-Lys | 3'5'Dmt | Lys | $NH_2$ |
| 3'5'Dmt | D-Lys | 3'5'Dmt | Orn | $NH_2$ |
| 3'5'Dmt | D-Lys | 3'5'Dmt | Dab | $NH_2$ |
| 3'5'Dmt | D-Lys | 3'5'Dmt | Dap | $NH_2$ |
| Tyr | D-Lys | Phe | Arg | $NH_2$ |
| Tyr | D-Orn | Phe | Arg | $NH_2$ |
| Tyr | D-Dab | Phe | Arg | $NH_2$ |
| Tyr | D-Dap | Phe | Arg | $NH_2$ |
| 2'6'Dmt | D-Arg | Phe | Arg | $NH_2$ |

TABLE 5-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides also include, but are not limited to, the aromatic-cationic peptides shown in Table 6.

TABLE 6

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexyl alanine

The amino acids of the peptides shown in Table 5 and 6 may be in either the L- or the D-configuration.

In some embodiments, the aromatic-cationic peptide is a peptide having:
  at least one net positive charge;
  a minimum of four amino acids;
  a maximum of about twenty amino acids;
  a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1.

In one embodiment, $2p_m$ is the largest number that is less than or equal to r+1, and a may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In one embodiment, the peptide comprises a tyrosine or a 2'6'-dimethyltyrosine (Dmt) residue at the N-terminus. For example, the peptide may have the formula Tyr-D-Arg-Phe-Lys-NH$_2$ or 2'6'-Dmt-D-Arg-Phe-Lys-NH$_2$. In another embodiment, the peptide comprises a phenylalanine or a 2'6'-dimethylphenylalanine residue at the N-terminus. For example, the peptide may have the formula Phe-D-Arg-Phe-Lys-NH$_2$ or 2'6'-Dmp-D-Arg-Phe-Lys-NH$_2$. In a particular embodiment, the aromatic-cationic peptide has the formula D-Arg-2'6'-Dmt-Lys-Phe-NH$_2$.

In one embodiment, the peptide is defined by formula I:

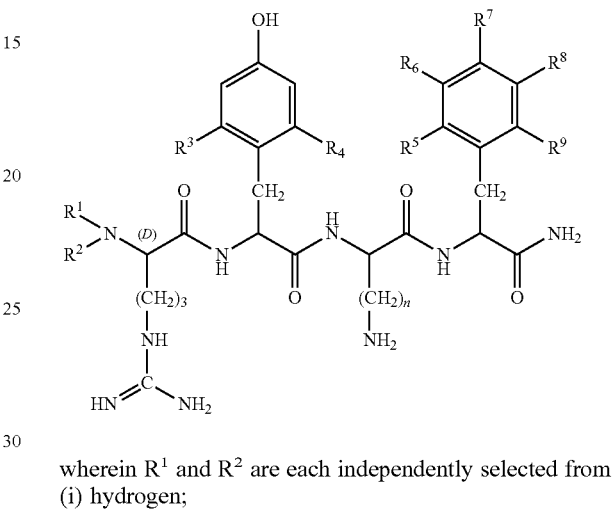

wherein $R^1$ and $R^2$ are each independently selected from
  (i) hydrogen;
  (ii) linear or branched $C_1$-$C_6$ alkyl;

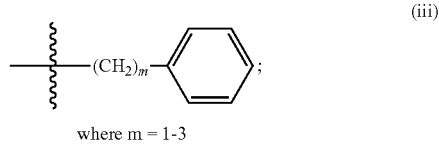

where m = 1-3

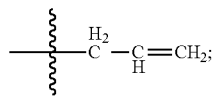

$R^3$ and $R^4$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo;
$R^5$, $R^6$, $R^7$, $R^8$, and $R^9$ are each independently selected from
  (i) hydrogen;
  (ii) linear or branched $C_1$-$C_6$ alkyl;
  (iii) $C_1$-$C_6$ alkoxy;
  (iv) amino;

(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In one embodiment, the peptide is defined by formula II:

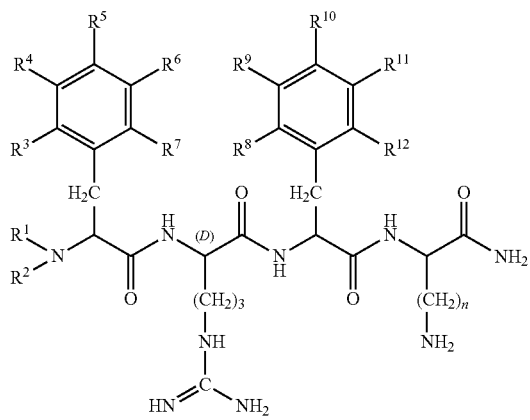

wherein $R^1$ and $R^2$ are each independently selected from
(i) hydrogen;
(ii) linear or branched $C_1$-$C_6$ alkyl;

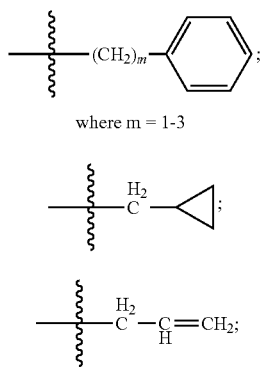

where m = 1-3

$R^3$, $R^4$, $R^5$, $R^6$, $R^7$, $R^8$, $R^9$, $R^{10}$, $R^{11}$ and $R^{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol*, 289, Academic Press, Inc, New York (1997).

Active Agents for Use in Combination Therapy with Aromatic-Cationic Peptides

In some aspects, the methods disclosed herein provide combination therapies for the treatment of atherosclerosis, and/or statin-related side effects comprising administering an effective amount of an aromatic-cationic peptide or a pharmaceutically acceptable salt thereof, such as acetate or trifluoroacetate salt, in combination with one or more active agents (therapeutic agents/active ingredients). Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In some embodiments, the combination therapy comprises administering to a subject in need thereof an aromatic-cationic peptide composition combined with one or more active agents, e.g., one or more antihyperlipidemic agent (e.g., a statin). In some embodiments, the antihyperlipidemic drug and the aromatic-cationic peptide are chemically linked.

Antihyperlipidemic (Hypolipidemic) Drugs and Statins

In some embodiments, the one or more additional active agents administered with one or more aromatic-cationic peptides disclosed herein (such as D-Arg-2'6'-Dmt-Lys-Phe-$NH_2$) or a pharmaceutically acceptable salt thereof, such as acetate or trifluoroacetate salt, is an antihyperlipidemic (hypolipidemic) drug. As used herein, the terms "antihyperlipidemic" and "hypolipedimic" are synonymous and are used interchangeably. For example, in some embodiments, the peptide D-Arg-2'6'-Dmt-Lys-Phe-$NH_2$ or a pharmaceutically acceptable salt thereof, such as acetate or trifluoroacetate salt is administered simultaneous to the antihyperlipidemic agent (drug). In some embodiments, the antihyperlipidemic drug and the aromatic-cationic peptide are chemically linked. In some embodiments, the peptide D-Arg-2'6'-Dmt-Lys-Phe-$NH_2$ or a pharmaceutically acceptable salt thereof, such as acetate or trifluoroacetate salt is administered prior to or subsequent to the antihyperlipidemic agent (drug).

In some embodiments, the antihyperlipidemic drug comprises one or more statins. In some embodiments, the statin is a combination drug comprising a statin and a non-statin. Exemplary, non-limiting statins include one or more of the following: lovastatin, (e.g., ADVICOR® (niacin extended-release/lovastatin), ALTOPREV™ (lovastatin extended-release), MEVACOR®), atorvastatin, (e.g., CADUET® (amlodipine and atorvastatin), LIPITOR®), rosuvastatin and/or rosuvastatin calcium, (e.g., CRESTOR®), simvastatin, (e.g., JUVISYNC® (sitagliptin/simvastatin), SIMCOR® (niacin extended-release/simvastatin), VYTORIN® (ezetimibe/simvastatin) and ZOCOR®), fluvastatin and/or fluvastatin sodium, (e.g., LESCOL®, LESCOL XL (fluvastatin extended-release)), pitavastatin (e.g., LIVALO®), pravastatin and/or pravastatin sodium (e.g., PRAVACHOL®)

In some embodiments, the hypolipidemic agent is a lipid lowering drug. In some embodiments, the active agent is an LDL lowering drug. In some embodiments, the active agent is a triglyceride lowering drug. In some embodiments, the active agent is an HDL elevating drug.

In some embodiments, the hypolipidemic agent is a cholesteryl ester transfer protein (CETP) inhibitor. In some embodiments, the CETP inhibitor is TORCETRAPIB®, ANACETRAPIB®, or DALCETRAPIB®.

In some embodiments, the hypolipidemic agent targets proprotein convertase subtilisin/kexin type 9 (PCSK9). In some embodiments, the agent is a PCSK9 inhibitor. In some embodiments, the agent inhibits PCSK9 function. In some embodiments, the agent inhibits PCSK9 expression. In some embodiments, the PCSK9 inhibitor targets PCSK9 mRNA. In some embodiments, the PCSK9 inhibitor is a PCSK9 siRNA. In some embodiments, the PCSK9 inhibitor is ALN-PCS or REGN727. In some embodiments, the one ore more therapies targeting PCSK9 is an anti-PCSK9 antibody. In some embodiments, the anti-PCSK9 antibody is a monoclonal antibody. In some embodiments, the anti-PCSK9 antibody is humanized. In some embodiments, the anti-PCSK9 antibody is a human antibody. In some embodiments, at least a portion of the framework sequence of the anti-PCSK9 antibody is a human consensus framework sequence. In some embodiments, the antibody is an antibody fragment selected from a Fab, Fab'-SH, Fv, scFv, or $Fab_2$ fragment.

In some embodiments, the hypolipidemic agent is a fibrate. In some embodiments, the fibrate is LIPOFEN® (fenofibrate), LOPID® (gemfibrozil), TRICOR® (fenofibrate), LOFIBRA® (fenofibrate), ATROMID-S® (clofibrate), TRILIPIX® (fenofibric acid), FENOGLIDE® (fenofibrate), ANTARA® (fenofibrate), FIBRICOR® (fenofibric acid), or TRIGLIDE® (fenofibrate). In some embodiments, the hypolipidemic agent is clinofibrate, simfibrate, benzafibrate.

In some embodiments, the hypolipidemic agent is niacin. In some embodiments, the niacin is NIASPAN®. In some embodiments, the niacin is NIACOR®.

In some embodiments, the hypolipidemic agent is a bile acid resin. In some embodiments, the bile acid resin is QUESTRAN®, QUESTRAN LIGHT®, COLESTID®, or WELCHOL®.

In some embodiments, the hypolipidemic agent prevents the absorption of dietary lipids. In some embodiments the agent is ezetimibe (e.g., ZETIA®), orlistat (e.g., XENICAL®), or a phytosterol.

In some embodiments, the hypolipidemic agent is a squalene synthase inhibitor. In some embodiments, the hypolipidemic agent is ApoA-1 MILANO®. In some embodiments, the hypolipidemic agent is AGI-1067. In some embodiments, the hypolipidemic agent is MIPOMERSEN®.

In some embodiments, the hypolipidemic agent is one or more of colestimide and colestyramine.

In some embodiments, the additional active agent administered in combination with an aromatic-cationic peptide of the present disclosure comprises an agent effective for apolipoprotein therapy. For example, in one aspect, the present disclosure provides combination therapies comprising administering an effective amount of peptide D-Arg-2'6'-Dmt-Lys-Phe-$NH_2$ or a pharmaceutically acceptable salt, such as acetate or trifluoroacetate salt in combination with one or more therapies targeting apolipoprotein (Apo). In some embodiments, the anti-Apo therapy is an antisense therapy. In some embodiments, the anti-Apo therapy is an antisense therapy targeting apolipoprotein B (Apo-B). In some embodiments, the anti-Apo-B antisense therapy is an antisense oligonucleotide, for example, comprising nucleotides linked with phosphorothioate linkages. In some embodiments, the anti-Apo-B antisense therapy is an antisense therapeutic that targets the messenger RNA for apolioprotein B MIPOMERSEN®. In some embodiments, the anti-Apo-B antisense therapy is KYNAMRO®. In some embodiments, the anti-Apo-B antisense therapy has the following sequence: G*-C*-C*-U*-C*-dA-dG-dT-dC-dT-dG-dmC-dT-dT-dmC-G*-C*-A*-C*-C*, where d=2'-deoxy, *=2'-O-(2-methoxyethyl), with 3'→5' phosphorothioate linkages. In some embodiments, the peptide D-Arg-2'6'-Dmt-Lys-Phe-$NH_2$ or a pharmaceutically acceptable salt thereof, such as acetate or trifluoroacetate salt is administered simultaneous to the anti-Apo-B agent. In some embodiments, the anti-Apo-B agent and the aromatic-cationic peptide are chemically linked. In some embodiments, the peptide D-Arg-2'6'-Dmt-Lys-Phe-$NH_2$ or a pharmaceutically acceptable salt thereof, such as acetate or trifluoroacetate salt is administered prior to or subsequent to the anti-Apo-B agent.

Statin Structure

As noted above, in some embodiments, the peptide D-Arg-2'6'-Dmt-Lys-Phe-$NH_2$ or a pharmaceutically acceptable salt thereof, such as acetate or trifluoroacetate salt is administered simultaneous to the statin. In some embodiments, the statin and the aromatic-cationic peptide are chemically linked. In some embodiments, the peptide D-Arg-2'6'-Dmt-Lys-Phe-$NH_2$ or a pharmaceutically acceptable salt, such as acetate or trifluoroacetate salt is administered prior to or subsequent to the statin. Typically, the structural components of statins include a dihydroxyheptanoic acid unit and a ring system with different substituents. The statin pharmacophore is modified hydroxyglutaric acid component, which is structurally similar to the endogenous substrate HMG CoA and the mevaldyl CoA transition state intermediate. The statin pharmacophore binds to the same active site as the substrate HMG-CoA and inhibits the HMG-CoA reductase enzyme. The HMG-CoA reductase enzyme is stereoselective and as a result functional statins typically have the 3R,5R stereochemistry.

Statins can be separated into two classes: type 1 (e.g. lovastatin, pravastatin, simvastatin) and type 2 (e.g. fluvastatin, cerivastatin, atorvastatin, rosuvastatin). Type 1 statins include a substituted decalin-ring structure that resemble mevastatin, a compound isolated from the mold *Penicillium citrinum*. Lovastatin was isolated from the mold *Aspergillus terreus* and pravastatin and simvastatin are chemically modified versions of lovastatin. Type 2 statins are fully synthetic and have larger substituent groups that interact with the HMG-CoA reductase enzyme. In addition, type 2 statins substitute fluorophenyl group for the butyryl group found on type 1 statins. The fluorophenyl group provides additional polar interactions typically resulting in tighter binding with the HMG-CoA reductase enzyme. Rosuvastatin has a sulfonamide group that is hydrophilic and increases binding affinity with the HMG-CoA reductase enzyme.

Atorvastatin Structure

Figure 6:
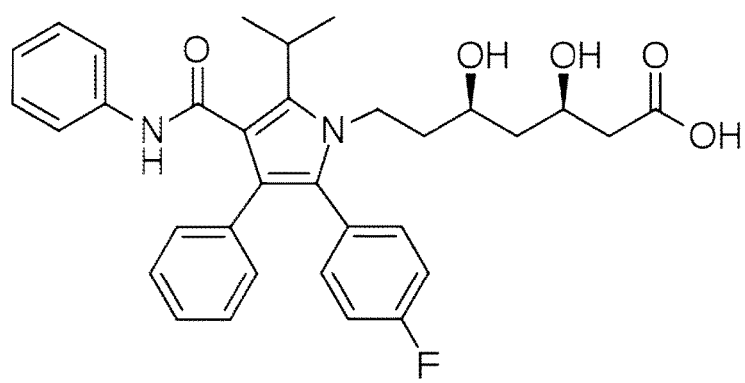
FIG. 6A is a diagram of the chemical structure of atorvastatin.
FIG. 6B is a diagram of the chemical structure of rosuvastatin.
Figure 6:
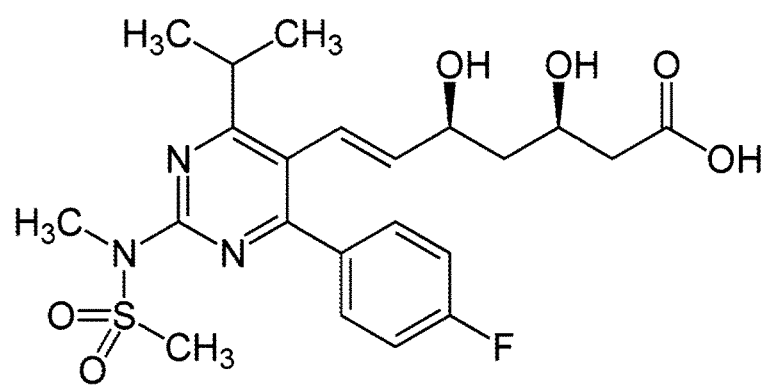

Atorvastatin is a ring-opened hydroxy-acid of trans-6-[2-(3- or 4-carboxamido-substituted pyrrol-1-yl)alkyl]-4-hydroxypyran-2-one (see e.g., FIG. 6A for the chemical structure). The general structure of atorvastatin and related compounds is provided in Formula I:

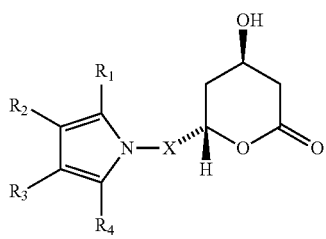

wherein X is —$CH_2$—, —$CH_2CH_2$—, —$CH_2CH_2CH_2$— or —$CH_2CH(CH_3)$.

$R_1$ is 1-naphthyl; 2-naphthyl; cyclohexyl; norbornenyl; 2-, 3-, or 4-pyridinyl; phenyl; phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms.

Either $R_2$ or $R_3$ is —$CONR_5R_6$ where $R_5$ and $R_6$ are independently hydrogen; alkyl of from one to six carbon atoms; 2-, 3-, or 4-pyridinyl; phenyl; phenyl substituted with fluorine, chlorine, bromine, cyano, trifluoromethyl, or carboalkoxy of from three to eight carbon atoms; and the other of $R_2$ or $R_3$ is hydrogen; alkyl of from one to six carbon atoms; cyclopropyl; cyclobutyl; cyclopentyl; cyclohexyl; phenyl; or phenyl substituted with fluorine, chlorine, bromine, hydroxyl; trifluoromethyl; alkyl of from one to four carbon atoms, alkoxy of from one to four carbon atoms, or alkanoyloxy of from two to eight carbon atoms.

$R_4$ is alkyl of from one to six carbon atoms; cyclopropyl; cyclobutyl; cyclopentyl; cyclohexyl; or trifluoromethyl.

Rosuvastatin Structure

Rosuvastatin is a compound related to the general structure set forth in formula II:

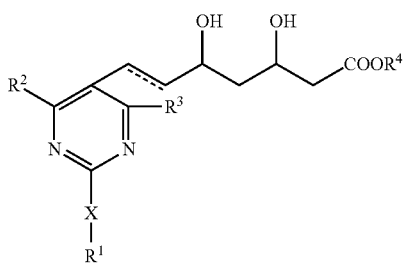

wherein $R_1$ is lower alkyl, aryl or aralkyl, each of which may have one or more substituents: $R_2$ and $R_3$ each is independently hydrogen, lower alkyl, or aryl, and each of said lower alkyl and aryl may have one or more substituents; $R_4$ is hydrogen, lower alkyl, or a cation capable of forming a non-toxic pharmaceutically acceptable salt; X is sulfur, oxygen, or sulfonyl, or imino which may have a substituent; the dotted line represents the presence or absence of a double bond, or the corresponding ring-closed lactone. (See e.g., FIG. 6B)

The term "lower alkyl" refers to a straight, branched, or cyclic $C_1$ to $C_6$ alkyl, including methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, and isohexyl and the like. Further, the lower alkyl may be substituted by 1 to 3 substituents independently selected from the group consisting of halogen, amino, and cyano. Halogen means fluorine, chlorine, bromine and iodine.

The term "aryl" refers to $C_6$ to $C_{12}$ aromatic group including phenyl, tolyl, xylyl, biphenyl, naphthyl, and the like. The aryl may have 1 to 3 substituents independently selected from the group consisting of lower alkyl, halogen, amino, and cyano. Preferred aryl is phenyl substituted by 1 to 3 halogens.

The term "aralkyl" refers to $C_1$ to $C_6$ lower alkyl substituted by $C_6$ to $C_{12}$ aromatic aryl group defined above. Examples of them are benzyl, phenethyl, phenylpropyl and the like, each of which may have 1 to 3 substituents independently selected from the group consisting of lower alkyl halogen, amino, cyano, and the like.

The term "a cation capable of forming a non-toxic pharmaceutically acceptable salt" refers to alkali metal ion, alkaline earth metal ion, and ammonium ion. Examples of alkali metal are lithium, sodium, potassium, and cesium, and examples of alkaline earth metal are beryllium, magnesium, and calcium. Especially, sodium and calcium are preferred.

Examples of "acyl" are formyl acetyl, propionyl, butyryl, isobutyryl, valeryl, and isovaleryl.

In the term "imino which may have a substituent," preferred substituents are acyl, optionally substituted amino, and substituted sulfonyl.

The term "substituted amino as substituent" means amino group substituted by sulfonyl and alkylsulfonyl. Examples of them are sulfonyl amino and methanesulfonyl amino.

The term "substituted sulfonyl as substituent" means sulfonyl group substituted by alkyl, amino, or alkylamino. Examples of them are methanesulfonyl, sulfamoyl, methylsulfamoyl, and N-methylsulfamoyl.

LIPITOR® and CRESTOR®

Atorvastatin (also known by the trademarked name LIPITOR®) can be used to reduce the risk of myocardial infarction, stroke, revascularization procedures, and angina in patients without coronary heart disease, but with multiple risk factors. Such risk factors include but are not limited to age, smoking, hypertension, low HDL-C, or a family history of early coronary heart disease. Atorvastatin can also be used to reduce the risk of myocardial infarction and stroke in patients with type 2 diabetes without coronary heart disease, but with multiple risk factors. Such risk factors include but are not limited to retinopathy, albuminuria, smoking, or hypertension. Atorvastatin can be used to reduce the risk of non-fatal MI, fatal and non-fatal stroke, revascularization procedures, hospitalization for coronary heart failure, and angina in patients with coronary heart disease. Atorvastatin can be used to reduce elevated total cholesterol, LDL-C, ApoB, and triglyceride levels and increase HDL-C in adult patients with primary hyperlipidemia (heterozygous familial and nonfamilal) and mixed dyslipidemia. Atorvastatin can be used to reduce elevated triglycerides in patients with hypertriglyceridemia and primary dysbetalipoproteinemia. Atorvastatin can also be used to reduce total cholesterol and LDL-C in patients with homozygous familial hypercholesterolemia (HoFH). Atorvastatin can be used to reduced elevated total cholesterol, LDL-C, and ApoB levels in boys and postmenarchal girls between the ages of 10-17, with heterozygous familial hypercholesterolemia after failing an adequate trial of diet therapy.

Atorvastatin has also been used to treat spinal cord injury in rodents, promoting locomotion and tissue sparing, as well as reducing inflammation when administered both pre- and post-injury. In addition, atorvastatin has been utilized in an in vitro model of hepatitis C virus (HCV) infection (alone and with interferon). In such a system, atorvastatin (as well as lovastatin, simvastatin, fluvastatin, and pitavastatin) was shown to have an anti-HCV effect. Accordingly, statins may be suitable for concurrent therapy with interferon.

Rosuvastatin (also known by the trade name CRESTOR®) can be used to treat patients with primary hyperlipidemia and mixed dyslipidemia as an adjunct to diet to reduce levels of total cholesterol, LDL-C, ApoB, non-HDL-C, and triglyceride levels and to increase levels of HDL-C. Rosuvastatin can also be used to treat patients with: hypertriglyceridemia as an adjunct to diet, primary dysbeta-lipoproteinemia (Type II hyperlipoproteinemia) as an adjunct to diet, and homozygous familial hypercholesterolemia (HoFH). Rosuvastatin can be used to slow the progression of atherosclerosis in patients as part of a treatment strategy to lower total cholesterol and LDL-C as an adjunct to diet. Rosuvastatin can be used to treat patients 10 to 17 years old with heterozygous familial hypercholesterolemia (HeFH) to reduce elevated total cholesterol, LDL-C, and ApoB after failing an adequate trial of diet therapy. Rosuvastatin can be used for reducing the risk of myocardial infarction, stroke, and arterial revascularization procedures in patients without evident coronary heart disease, but with multiple risk factors. Such risk factors include hypertension, low HDL-C, smoking, or a family history of premature coronary heart disease.

Therapeutic Uses of Aromatic-Cationic Peptides and Active Agents

Atherosclerosis

The aromatic-cationic peptides described herein are useful to prevent or treat disease such as atherosclerosis. The combination of peptides and active agents such as those described above (e.g., antihyperlipedimic agents such as statins) are useful in treating any atherosclerosis, as well as the signs, symptoms or complications of atherosclerosis. Atherosclerosis (also known as arteriosclerotic vascular disease or ASVD) is a condition in which an artery wall thickens as a result of the accumulation of fatty materials such as cholesterol. Atherosclerosis is a chronic disease that can remain asymptomatic for decades. It is a syndrome affecting arterial blood vessels, a chronic inflammatory response in the walls of arteries, caused largely by the accumulation of macrophage white blood cells and promoted by low-density lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

The pathobiology of atherosclerotic lesions is complicated but generally, stable atherosclerotic plaques, which tend to be asymptomatic, are rich in extracellular matrix and smooth muscle cells, while unstable plaques are rich in macrophages and foam cells and the extracellular matrix separating the lesion from the arterial lumen (also known as the fibrous cap) is usually weak and prone to rupture. Ruptures of the fibrous cap expose thrombogenic material, such as collagen to the circulation and eventually induce thrombus formation in the lumen. Upon formation, intraluminal thrombi can occlude arteries outright (e.g., coronary occlusion), but more often they detach, move into the circulation and can eventually occlude smaller downstream branches causing thromboembolism (e.g., stroke is often caused by thrombus formation in the carotid arteries). Apart from thromboembolism, chronically expanding atherosclerotic lesions can cause complete closure of the lumen. Chronically expanding lesions are often asymptomatic until lumen stenosis is so severe that blood supply to downstream tissue(s) is insufficient resulting in ischemia.

These complications of advanced atherosclerosis are chronic, slowly progressive and cumulative. In some instances, soft plaques suddenly rupture, causing the formation of a thrombus that will rapidly slow or stop blood flow, leading to death of the tissues fed by the artery (infarction). Coronary thrombosis of a coronary artery is also a common complication which can lead to myocardial infarction. Blockage of an artery to the brain may result in stroke. In advanced atherosclerotic disease, claudication from insufficient blood supply to the legs, typically caused by a combination of both stenosis and aneurysmal segments narrowed with clots, may occur.

Atherosclerosis can affect the entire artery tree, but larger, high-pressure vessels such as the coronary, renal, femoral, cerebral, and carotid arteries are typically at greater risk.

Signs, symptoms and complications of atherosclerosis include, but are not limited to increased plasma total cholesterol, VLDL-C, LDL-C, free cholesterol, cholesterol ester, triglycerides, phospholipids and the presence of lesions (e.g., plaques) in arteries, as discussed above. In some embodiments, increased cholesterol (e.g., total cholesterol, free cholesterol and cholesterol esters) can be seen in one or more of plasma, aortic tissue and aortic plaques.

Predisposion to atherosclerosis is also a concern. Accordingly, the present disclosure relates to methods of administering aromatic-cationic peptides alone, or in combination with one or more antihyperlipidemic agents (e.g., statins), to prevent atherosclerosis, or the signs, symptoms or complications thereof. In some embodiments a subject predisposed to atherosclerosis may exhibit one or more of the following characteristics: advanced age, a family history of heart disease, a biological condition, high blood cholesterol. In some embodiments, the biological condition comprises high levels of low-density lipoprotein cholesterol (LDL-C) in the blood, low levels of high-density lipoprotein cholesterol (HDL-C) in the blood, hypertension, insulin resistance, diabetes, excess body weight, obesity, sleep apnea, lifestyle choice and/or a behavioral habit. In some embodiments, the behavioral habit comprises smoking and/or alcohol use. In some embodiments, the lifestyle choice comprises an inactive lifestyle and/or a high stress level.

Statin-related Side Effects

In some embodiments, aromatic-cationic peptides of the present disclosure (e.g., D-Arg-2'6'-Dmt-Lys-Phe-NH$_2$), or a pharmaceutically acceptable salt thereof such as acetate salt or trifluoroacetate salt, are administered with one or more hypolipidemic agents (e.g., statins). In some embodiments, the statin and the aromatic-cationic peptide are chemically linked. In some embodiments, the aromatic-cationic peptides of the present disclosure delay onset, ameliorate, inhibit or eliminate the side-effects and/or toxicity of hypolipeidemic agent (e.g., statin). In some embodiments, the peptides ameliorate organ damage caused by hypolipidemic agents (e.g., statins). In some embodiments, the peptides ameliorate liver damage, kidney damage, renal toxicity or rhabdomyolysis. In some embodiments, the peptides ameliorate symptoms associated with the toxic side effects of hypolipidemic agents, including but not limited to muscle weakness, muscle tenderness, malaise, headache, fever, dark urine, nausea, and vomiting.

Hypolipidemic Agent Dosage

In some embodiments, administration of aromatic-cationic peptides of the present technology in conjunction with one or more hypolipidemic agents (e.g., statins), permits a higher dose of the hypolipidemic agent to be administered to a subject than would otherwise be tolerated by the subject. Also disclosed herein are methods for increasing an antihyperlipidemic agent (such as a statin) dose in a subject in need thereof, or allowing administration of an antihyperlipidemic agent (such as a statin) to a subject who would normally be contraindicated for e.g., statin treatment (e.g., in a subject who exhibits negative side effects related to statin administration at an effective dose). Exemplary negative side effects are described above and in more detail below, and include but are not limited to muscle weakness and organ damage.

In some embodiments, by ameliorating the toxic or negative side effects of the hypolipidemic agent, the dose of hypolipidemic agent may be increased to a level sufficient to achieve a target blood lipid level.

In some embodiments, the target blood lipid level is a total cholesterol level. In some embodiments, the target cholesterol level is less than about 200 mg/dL. In some embodiments, the target cholesterol level is from about 130 to about 200 mg/dL. In some embodiments, the target cholesterol level is less than about 200, less than about 190, less than about 180, less than about 170, less than about 160, less than about 150, less than about 140, or less than about 130 mg/dL.

Additionally or alternatively, in some embodiments, the target blood lipid level is a target LDL level. In some embodiments, the target LDL level is less than about 100 mg/dL. In some embodiments, the target LDL level is from about 50 to about 100 mg/dL. In some embodiments, the target LDL level is less than about 100, less than about 90, less than about 80, less than about 70, less than about 60, or less than about 50 mg/dL.

Additionally or alternatively, in some embodiments, the target blood lipid level is a target HDL level. In some embodiments, the target HDL level is greater than about 60 mg/dL. In some embodiments, the target HDL level is from about 30 to about 65 mg/dL. In some embodiments, the target HDL level is greater than about 30, greater than about 35, greater than about 40, greater than about 45, greater than about 50, greater than about 55, greater than about 60, or greater than about 65 mg/dL.

Additionally or alternatively, in some embodiments, the target blood lipid level is a target triglyceride level. In some embodiments, the target triglyceride level is less than about 200 mg/dL. In some embodiments, the target triglyceride level is from about 140 to about 200 mg/dL. In some embodiments, the target triglyceride level is less than about 140, less than about 150, less than about 160, less than about 170, less than about 180, less than about 190, or less than about 200 mg/dL.

By way of example, but not by way of limitation, in some embodiments, a subject with an unsuitable/unhealthy lipid level is administered a first dosage level of an anithyperlipidemic agent (e.g., a statin) to achieve a target lipid level, in combination with a first dosage level of an aromatic-cationic peptide of the present disclosure (e.g., D-Arg-2'6'-Dmt-Lys-Phe-NH$_2$) at t=0. In some embodiments, the subject is administered the anithyperlipidemic agent, or is administered an anithyperlipidemic agent and a peptide at the first dosage level for 1 day, 2 days, 3 days, 4 days, 5 days, 1 week, 2 weeks, 3 weeks, 1 month, 2 months, 3 months, 4 months, 6 months, 1 year, 2 years, 3 years, 4 years, 5 years or 10 years. In some embodiments, the subject is administered the anithyperlipidemic agent, or is administered an anithyperlipidemic agent and a peptide at the first dosage level once per day, twice per day, every other day, once every third day, fourth day, fifth day, once per week, or once every other week. In some embodiments, the antihyperlipidemic agent and the aromatic-cationic peptide are chemically linked.

At a later time (t=1) (e.g., 1 day, 2 days, 3 days, 4 days, 5 days, 1 week, 2 weeks, 3 weeks, 1 month, 2 months, 3 months, 6 months, 1 year or 2 years) after taking the anithyperlipidemic agent, or the anithyperlipidemic agent and the peptide at the first dosage level, the subject's lipid levels and any negative or toxic side effects characteristic of the anithyperlipidemic agent are evaluated. In some embodiments, due to the positive effects of the peptpide, the subject exhibits no negative or toxic side effects of the anithyperlipidemic agent. In some embodiments, the dosage level of the antihyperlipidemic agent is increased to a second dosage level to more quickly or effectively achieve an acceptable (e.g., target) lipid level. In some embodiments, the peptide dosage level remains constant, e.g., is equal to the first dosage level. In some embodiments, the peptide dosage level is increased, e.g., is greater than the first dosage level. In some embodiments, the peptide dosage level is decreased, e.g., is less than the first dosage level. In some embodiment, no additional peptide is administered with the second dosage level of the antihyperlipidemic agent. In some embodiments, peptide is administered as often as the antihyperlipidemic agent. In some embodiments, the peptide is administered more or less frequently than the antihyperlipidemic agent. In some embodiments, the antihyperlipidemic agent and the aromatic-cationic peptide are chemically linked.

In some embodiments, the subject's lipid levels and any negative or toxic side effects characteristic of the anithyperlipidemic agent are evaluated at t=2, t=3, etc. In some embodiments, the dosage level of the antihyperlipidemic agent is increased to a third, fourth, fifth, etc. dosage level to more quickly or effectively achieve a target lipid level. In some embodiments, at t=2, 3, etc. the peptide dosage level may decreased, increased, remain the same (e.g., first dosage level) or be omitted from one or more administrations.

Coenzyme Q10 Levels

The statins (simvastatin, lovastatin, pravastatin, fluvastatin and the like) are hydroxy-methylglutaryl coenzyme A (HMG-CoA) reductase inhibitors. By inhibiting this enzyme, statins reduce the synthesis of mevalonate, an intermediary in the cholesterol synthesis pathway. The same biosynthetic pathway is shared by coenzyme Q10; mevalonate is also a precursor of coenzyme Q10. Thus, both cholesterol and coenzyme Q10 biosynthesis decrease with statin treatment.

Some of the side effects of statins include mitochondrial dysfunction, decreased coenzyme Q10 levels, a variety of myopathies (ranging from mild myalgia to fatal rhabdomyolysis), diabetes, kidney failure and memory loss. Additional side effects include fever, dark colored urine, swelling, weight gain, changes in urination frequency, dry mouth, drowsiness, nausea, diarrhea, jaundice, loss of appetite, insomnia, and headache.

Coenzyme Q10 (CoQ10) is a naturally occurring, fat-soluble quinone that is localized in hydrophobic portions of cellular membranes. Approximately half of the body's CoQ10 is obtained through dietary fat ingestion, whereas the remainder results from endogenous synthesis. Coenzyme Q10 participates in electron transport during oxidative phosphorylation in mitochondria, protects against oxidative stress produced by free radicals, and regenerates active forms of the antioxidants ascorbic acid and tocopherol (vitamin E). Given the role of CoQ10 in mitochondrial energy production and the importance of mitochondria in muscle function, it is likely that statin-induced CoQ10 deficiency plays a role in statin-associated mitochondrial dysfunction and myopathies (e.g., rhabdomyolysis). Without wishing to be bound by theory, it is also possible that CoQ10 plays a role in additional statin-induced side effects, such as but not limited to memory loss, kidney failure and diabetes.

Figure 5:
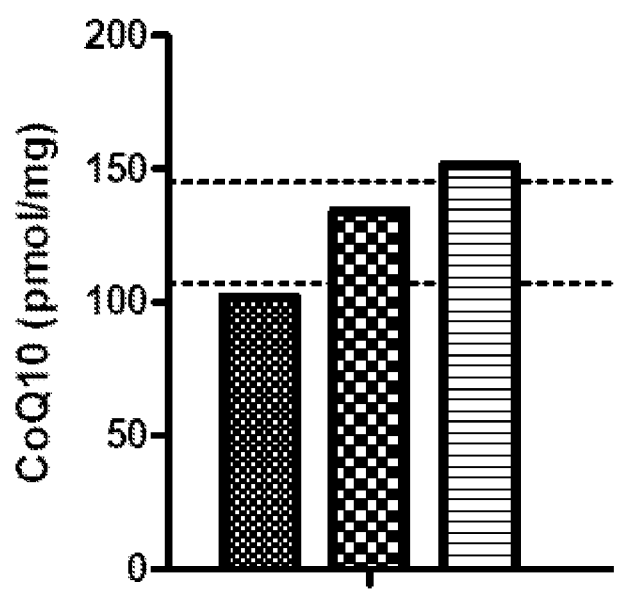
FIG. 5 is a graph showing the effect of the aromatic-cationic peptide D-Arg-2'6'-Dmt-Lys-Phe-NH₂ on coenzyme Q10 levels in fibroblast cells. The first bar represents saline treated fibroblasts; the second bar represents fibroblasts treated with 10 nM peptide for 16-24 hours; the third bar represents fibroblasts treated with 10 nM peptide for 5 days.

As shown in Example 3 and FIG. 5, aromatic-cationic peptides of the present disclosure increase CoQ10 levels in fibroblast cells. Accordingly, in some embodiments, aromatic-cationic peptides of the present disclosure are administered with one or more statins to alleviate or prevent the myopathic side effects of statin administration. The peptide may be administered before, simultaneously with, or after statin administration. The reason for statin administration is not intended to limit peptide administration. That is, the subject may be suffering from, or at risk for, any number of disease, conditions or illnesses for which one or more statins are indicated.

By way of example, but not by way of limitation, exemplary diseases, conditions, risk factors, characteristics, or reasons for administering a statin include one or more of the following: advanced age, smoking, hypertension, low HDL-C, a family history of early coronary heart disease, an increased risk of myocardial infarction and stroke in subjects with type 2 diabetes without coronary heart disease, but with other or multiple risk factors (e.g., retinopathy, albuminuria, smoking, or hypertension), to reduce the risk of non-fatal MI, fatal and non-fatal stroke, revascularization procedures, hospitalization for coronary heart failure, or angina in patients with coronary heart disease, to reduce elevated total cholesterol, LDL-C, ApoB, and triglyceride levels and increase HDL-C in adult patients with primary hyperlipidemia (heterozygous familial and nonfamilal) and mixed dyslipidemia, to reduce elevated triglycerides in patients with hypertriglyceridemia and primary dysbetalipoproteinemia, to reduce total cholesterol and LDL-C in patients with homozygous familial hypercholesterolemia (HoFH), to reduce elevated total cholesterol, LDL-C, and ApoB levels in boys and postmenarchal girls between the ages of 10-17, with heterozygous familial hypercholesterolemia after failing an adequate trial of diet therapy, to treat patients with primary hyperlipidemia and mixed dyslipidemia as an adjunct to diet to reduce levels of total cholesterol, LDL-C, ApoB, nonHDL-C, and triglyceride levels and to increase levels of HDL-C, to treat patients with: hypertriglyceridemia as an adjunct to diet, primary dysbetalipoproteinemia (Type III hyperlipoproteinemia) as an adjunct to diet, and homozygous familial hypercholesterolemia (HoFH), to slow the progression of atherosclerosis in patients as part of a treatment strategy to lower total cholesterol and LDL-C as an adjunct to diet, to treat patients 10 to 17 years old with heterozygous familial hypercholesterolemia (HeFH) to reduce elevated total cholesterol, LDL-C, and ApoB after failing an adequate trial of diet therapy, to reduce the risk of myocardial infarction, stroke, and arterial revascularization procedures in patients without evident coronary heart disease, but with multiple risk factors (e.g., hypertension, low HDL-C, smoking, or a family history of premature coronary heart disease), to reduce inflammation, promote locomotion, and promote tissue sparing in spinal cord injury, and/or to reduce or eliminate infection of HCV in a patient.

In addition, in some embodiments, the administration of one or more aromatic-cationic peptides of the present disclosure in combination with one or more antihyperlipidemic agents (e.g., statins) will allow the subject to receive a higher dose of one or more antihyperlipidemic agents to alleviate a disease, conditions, or a sign, symptom or characteristic of a disease or condition. By way of example but not by way of limitation, the label on the statin CRESTOR® emphasizes the risks (e.g., myopathy, rhabdomyolysis and various forms of kidney failure) at the highest approved does of 40 mg, and recommends administration of lower doses. By administering an aromatic-cationic peptide with the antihyperlipidemic agent, the detrimental side effects seen with higher dosages may delayed, ameliorated or eliminated, thereby allowing for administration of the higher therapeutic antihyperlipidemic (e.g., statin) dose. In some embodiments, the anithyperlipidemic agent and the aromatic-cationic peptide are chemically linked.

General

The disclosure also provides for both prophylactic and therapeutic methods of treating a subject having or at risk of (or susceptible to) atherosclerosis and related complications. Accordingly, the present methods provide for the prevention and/or treatment of atherosclerosis in a subject by administering an effective amount of an aromatic-cationic peptide and one or more active agents, such as an antihyperlipidemic drug (e.g., a statin) to a subject in need thereof. In some embodiments, the anithyperlipidemic agent and the aromatic-cationic peptide are chemically linked.

In various embodiments, suitable in vitro or in vivo assays are performed to determine the effect of a specific combination of aromatic-cationic peptides and one or more active agents and whether its administration is indicated for treatment. In various embodiments, assays can be performed with representative animal models to determine if a given aromatic-cationic peptide and cardiovascular agent treatment regime exerts the desired effect in preventing or treating atherosclerosis. Compounds for use in therapy can be tested in suitable animal model systems including, but not limited to rats, mice, chicken, pigs, cows, monkeys, rabbits, and the like, prior to testing in human subjects. Any of the animal model systems known in the art can be used prior to administration to human subjects.

In therapeutic applications, compositions or medicaments are administered to a subject suspected of, or already suffering from such a disease in an amount sufficient to cure, or at least partially arrest, the symptoms of the disease, including its complications and intermediate pathological phenotypes in development of the disease. As such, the invention provides methods of treating an individual afflicted with atherosclerosis.

Modes of Administration, Formulations and Effective Dosages

Formulations

Any method known to those in the art for contacting a cell, organ or tissue with a peptide and active agent may be employed. Suitable methods include in vitro, ex vivo, or in vivo methods. In vivo methods typically include the administration of an aromatic-cationic peptide and active agent, such as those described above, to a mammal, suitably a human. When used in vivo for therapy, the aromatic-cationic peptides and active agents may be administered to the subject in effective amounts (i.e., amounts that have desired therapeutic effect). The dose and dosage regimen will depend upon the degree of the injury in the subject, the characteristics of the particular aromatic-cationic peptide and/or active agent used, e.g., its therapeutic index, the subject, and the subject's history.

The effective amount may be determined during preclinical trials and clinical trials by methods familiar to physicians and clinicians. An effective amount of a peptide and one or more additional active agents useful in the methods may be administered to a mammal in need thereof by any of a number of well-known methods for administering pharmaceutical compounds. The peptide may be administered systemically or locally.

The compound may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the pharmaceutically acceptable salt is acetate or trifluoroacetate salt.

The compounds described herein can be incorporated into pharmaceutical compositions for administration, singly or in combination, to a subject for the treatment or prevention of a disorder described herein. Such compositions typically include the active agent (e.g., peptide and one or more active agents, e.g., a statin) and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof Oral compositions generally include an inert diluent or an edible carrier. For the purpose of oral therapeutic administration, the active compounds can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include, but are not limited to those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in, but not limited to U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Formulations Linking Peptides and Additional Active Agents—Combination Therapy

In some embodiments, at least one additional active agent, e.g., an antihyperlipidemic agent (e.g., statin), and at least one aromatic cationic peptide as described above (e.g., D-Arg-2'6'-Dmt-Lys-Phe-NH$_2$ or a pharmaceutically acceptable salt thereof), are associated to form a complex. The antihyperlipidemic agent and aromatic-cationic peptide can associate by any method known to those in the art. The following examples of peptide/active agent linkages are provided by way of illustration only, and are not inteneded to be limiting. In general, additional active agents can be linked to an aromatic-cationic peptide of the present disclosure by any suitable technique, with appropriate consideration of the need for pharmokinetic stability and reduced overall toxicity to the subject. A therapeutic agent can be coupled to an aromatic-cationic peptide either directly or indirectly (e.g., via a linker group).

Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking. In some embodiments, bonds between the compounds are rapidly degraded or dissolved; in some embodiments, bonds are cleaved by drug metabolizing or excretatory chemistry and/or enzymes.

For a chemical bond or physical bond, a functional group on the molecule typically associates with a functional group on the aromatic cationic peptide. For example, hypolipidemic agents such as statins often contain a carboxyl functional group, as well as hydroxyl functional groups. The free amine group of an aromatic cationic peptide may be cross-linked directly to the carboxl group of a statin using 1-Ethyl-3-[3-dimethylaminopropyl]carbodiimide hydrochloride (EDC or EDAC) or dicyclohexylcarbodiimide (DCC). Cross-linking agents can, for example, be obtained from Pierce Biotechnology, Inc., Rockford, Ill. The Pierce Biotechnology, Inc. website can provide assistance.

In some embodiments, a direct reaction between an additional active agent (e.g., an antihyperlipidemic agent) and an aromatic-cationic peptide (e.g., D-Arg-2'6'-Dmt-Lys-Phe-NH$_2$ or a pharmaceutically acceptable salt thereof), is formed when each possesses a functional group capable of reacting with the other. For example, a nucleophilic group, such as an amino or sulfhydryl group, can be capable of reacting with a carbonyl-containing group, such as an anhydride or an acid halide, or with an allyl group containing a good leaving group (e.g., a halide). Additionally or alternatively, a suitable chemical linker group can be used. A linker group can function as a spacer to distance the peptide and the additional active agent in order to avoid interference with, for example, binding capabilities. A linker group can also serve to increase the chemical reactivity of a substituent, and thus increase the coupling efficiency.

In exemplary embodiments, suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups can be designed into recombinant immunoglobulin molecules. It will be evident to those skilled in the art that a variety of bifunctional or polyfunctional reagents, both homo- and hetero-functional (such as those described in the catalogue of the Pierce Chemical Co., Rockford, Ill.), can be employed as a linker group. Coupling can be affected, e.g., through amino groups, carboxyl groups, sulfhydryl groups or oxidized carbohydrate residues (see, e.g., U.S. Pat. No. 4,671,958).

As an additional or alternative coupling method, an additional active agent can be coupled to the aromatic-cationic peptides disclosed herein, e.g., through an oxidized carbohydrate group at a glycosylation site, for example, as described in U.S. Pat. Nos. 5,057,313 and 5,156,840. Yet another alternative method of coupling an aromatic cationic peptide to an additional active agent is by the use of a non-covalent binding pair, such as streptavidin/biotin, or avidin/biotin. In these embodiments, one member of the pair is covalently coupled to the aromatic-cationic peptide, and the other member of the binding pair is covalently coupled to the additional active agent.

In some embodiments, an additional active agent may be more potent when free from the aromatic-cationic peptide, and it may be desirable to use a linker group which is cleavable during or upon internalization into a cell, or which is gradually cleavable over time in the extracellular environment. A number of different cleavable linker groups have been described. Examples of the intracellular release of active agents from these linker groups include, e.g., but are not limited to, cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

In some embodiments, an aromatic-cationic peptide as disclosed herein is coupled to more than one active agent. For example, in some embodiments, aromatic-cationic peptide is coupled to a mixture of at least two additional active agents. That is, more than one type of active agent can be coupled to one aromatic-cationic peptide. For instance, a therapeutic moiety, such as a an antihyperlipidemic agents such as a statin, polynucleotide, antibody or antisense sequence, can be conjugated to an aromatic-cationic peptide to increase the effectiveness of the therapy, as well as lowering the required dosage necessary to obtain the desired therapeutic effect. Regardless of the particular embodiment, formulations with more than one moiety can be prepared in a variety of ways. For example, more than one moiety can be coupled directly to an aromatic-cationic peptide, or linkers that provide multiple sites for attachment (e.g., dendrimers) can be used. Alternatively, a carrier with the capacity to hold more than one active agent can be used.

As explained above, an aromatic-cationic peptide can be linked to additional active agents in a variety of ways, including covalent bonding either directly or via a linker group, and non-covalent associations. For example, in some embodiments, the aromatic-cationic peptide and additional active agents can be combined with encapsulation carriers. In some embodiments, this is especially useful to allow the therapeutic compositions to gradually release the aromatic-cationic peptide and additional active agent over time while concentrating it in the vicinity of the target cells.

In some embodiments, linkers that that are cleaved within a cell may also be used. For example, heterocyclic "self-immolating" linker moieties can be used to link aromatic cationic peptides of the present invention to additional active agents such as antihyperlipidemic drugs, such as statins (see, for example U.S. Pat. No. 7,989,434 and U.S. Pat. No. 8,039,273, incorporated herein by reference).

In some embodiments, the linker moiety comprises a heterocyclic "self-immolating moiety" bound to the aromatic-cationic peptide (e.g., D-Arg, 2'6'-Dmt-Lys-Phe-NH$_2$) and an additional active agent (e.g., an antihyperlipidemic agent such as a statin) and incorporates an amide group or beta-glucuronide group that, upon hydrolysis by an intracellular protease or beta-glucuronidase, initiates a reaction that ultimately cleaves the self-immolative moiety from the aromatic cationic peptide such that the additional active agent (e.g., statin) is released from the peptide in an active form.

Figure 12:
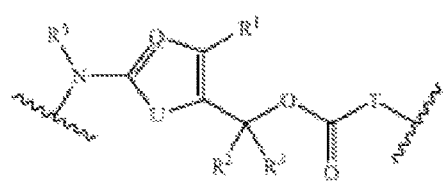
FIG. 12 shows exemplary self immolating moieties.
Figure 12:
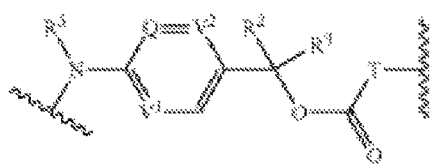
Figure 12:
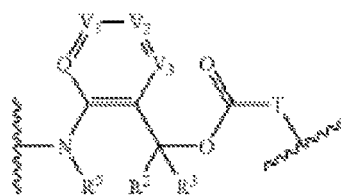

Exemplary self immolating moieties include those of Formulas I, II, and III, presented in FIG. 12. In FIG. 12, the wavy lines indicate the covalent attachment sites to the aromatic cationic peptide and the statin, wherein:

U is O, S or $NR^6$;

Q is $CR^4$ or N;

$V^1$, $V^2$ and $V^3$ are independently $CR^4$ or $V^1$ provided that for formula II and III at least one of Q, $V^1$ and $V^2$ is N;

T is NH, $NR^6$, O or S pending from said drug moiety;

$R^1$, $R^2$, $R^3$ and $R^4$ are independently selected from H, F, Cl, Br, I, OH, $-N(R^5)_2$, $-N(R^5)_3{}^+$, $C_1$-$C_8$ alkylhalide, carboxylate, sulfate, sulfamate, sulfonate, $-SO_2R^5$, $-S(=O)R^5$, $-SR^5$, $-SO_2N(R^5)_2$, $-C(=O)R^5$, $-CO_2R^5$, $-C(=O)N(R^5)_2$, $-CN$, $-N_3$, $-NO_2$, $C_1$-$C_8$ alkoxy, $C_1$-$C_8$ halosubstituted alkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, $R^2$ and $R^3$ form a carbonyl (=O), or spiro carbocyclic ring of 3 to 7 carbon atoms; and $R^5$ and $R^6$ are independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, $-N(R^5)_2$, $-N(R^5)_3{}^+$, $C_1$-$C_8$ alkylhalide, carboxylate, sulfate, sulfamate, sulfonate, $C_1$-$C_8$alkylsulfonate, $C_1$-$C_8$ alkylamino, 4-dialkylaminopyridinium, $C_1$-$C_8$ alkylhydroxyl, $C_1$-$C_8$ alkylthiol, $-SO_2R^5$, $-S(=O)R^5$, $-SR^S$, $-SO_2N(R^5)_2$, $-C(=O)R^5$, $-CO_2R^5$, $-C(=O)N(R^5)_2$, $-CN$, $-N_3$, $-NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate.

The linker moiety may further include a cleavable peptide sequence adjacent to the self-immolative moiety that is a substrate for an intracellular enzyme, for example a cathepsin such as cathepsin B, that cleaves the cleavable peptide at the amide bond shared with the self-immolative moiety (e.g. Phe-Lys, Ala-Phe, or Val-Cit). In some embodiments, the amino acid residue chain length of the cleavable peptide sequence ranges from that of a single amino acid to about eight amino acid residues. The following are exemplary enzymatically-cleavable peptide sequences: Gly-Gly, Phe-Lys, Val-Lys, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Ala-Phe, Gly-Gly-Gly, Gly-Ala-Phe, Gly-Val-Cit, Gly-Phe-Leu-Gly, Ala-Leu-Ala-Leu, Phe-N 9-tosyl-Arg, and Phe-N 9-Nitro-Arg, in either orientation. Numerous specific cleavable peptide sequences suitable for use in the present formulations can be designed and optimized in their selectivity for enzymatic cleavage by a particular intracellular enzyme, e.g. liver cell enzymes.

A spacer unit may be linked to the aromatic cationic peptide via an amide, amine or thioether bond. The additional active agent (e.g., an antihyperlipidemic agent such as a statin) may be connected to the self-immolative moiety of the linker via a chemically reactive functional group pending from the additional active agent, such as a primary or secondary amine, hydroxyl, or carboxyl group.

Additionally or alternatively, the self-immolative linkers described herein can be used to link aromatic-cationic peptides to antibodies, nucleic acids or other biologically active molecules (e.g., antihyperlipidemic agents). For example, an aromatic cationic peptide with or without a spacer may be attached to a linker that includes a cleavable peptide sequence or beta-glucuronide group and a self-immolative linker attached to an antibody, e.g., an antibody that reduces LDL-C, such as an antibody against a PCSK9 inhibitor and/or an anti-ApoB agent, such as an antisense RNA.

Figure 13:
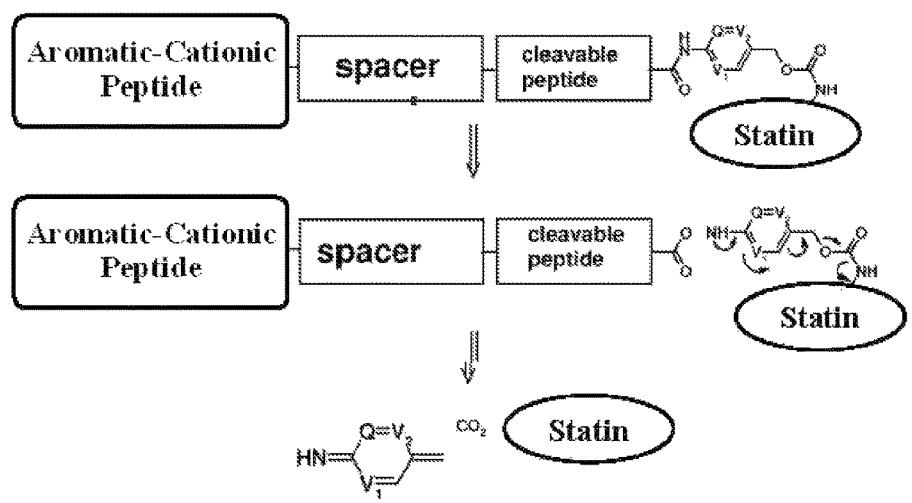
FIGS. 13A and 13B show exemplary schematics for formulations linking an aromatic-cationic peptide to a statin (A); and linking an aromatic-cationic peptide to an antibody (B).
FIGS. 13C and 13D show exemplary schematics for formulations linking an aromatic-cationic peptide to a anti-hyperlipidemic drug (C); and linking an aromatic-cationic peptide to an antibody (D).
Figure 13:
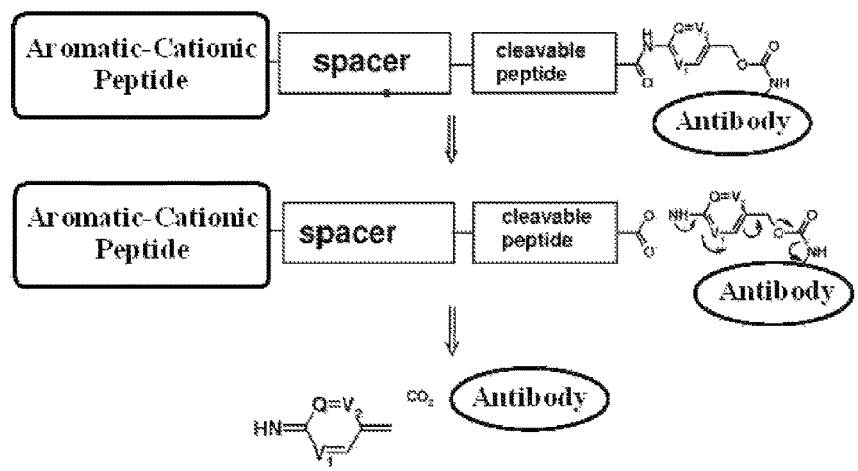

Exemplary schematics of illustrative embodiments of such formulations are shown in FIG. 13.

In some embodiments, once the statin-peptide complex enters the cell or blood stream, the linker is cleaved releasing the peptide from the antihyperlipidemic agent (e.g., a statin). The formulations are not intended to be limited by linkers or cleavage means. For example, in some embodiments, linkers are cleaved in the body (e.g., in the blood stream, interstitial tissue, gastrointestinal tract, etc.), releasing the peptide from the second active agent (e.g., an antihyperlipidemic drug such as a statin) via enzymes (e.g., esterases) or other chemical reactions.

Figure 7:
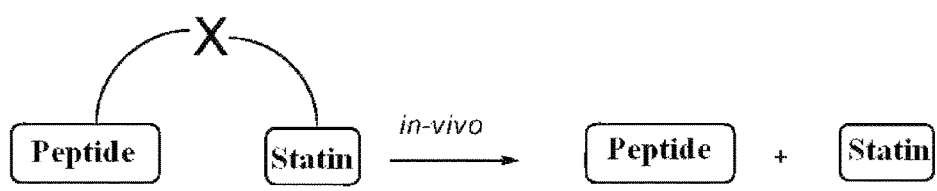
FIG. 7A is a schematic diagram illustrating linkage of the peptide D-Arg-2'6'-Dmt -Lys-Phe-NH₂ to statins using a labile bond such that in vivo hydrolysis of the pro-drug releases the two pharmaceutically active agents.
FIG. 7B is a schematic diagram illustrating linkage of the peptide D-Arg-2'6'-Dmt-Lys-Phe-NH₂ to a hypolipidemic drug using a labile bond such that in vivo hydrolysis of the pro-drug releases the two pharmaceutically active agents.
Figure 7:
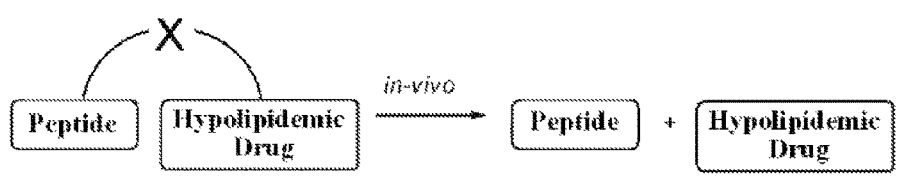
Figure 8:
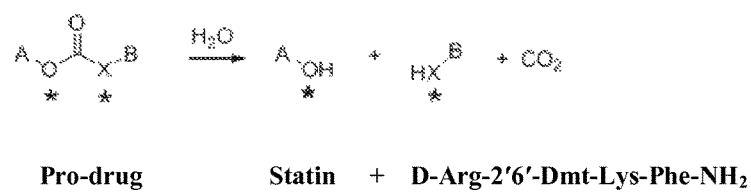
FIGS. 8A and 8B show illustrative embodiments where when X=O, a carbonate-linked pro-drug is formed.
Figure 8:
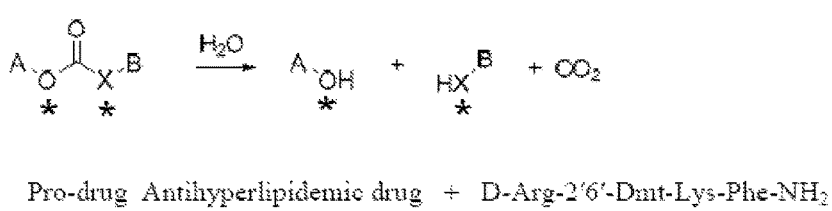
Figure 9:
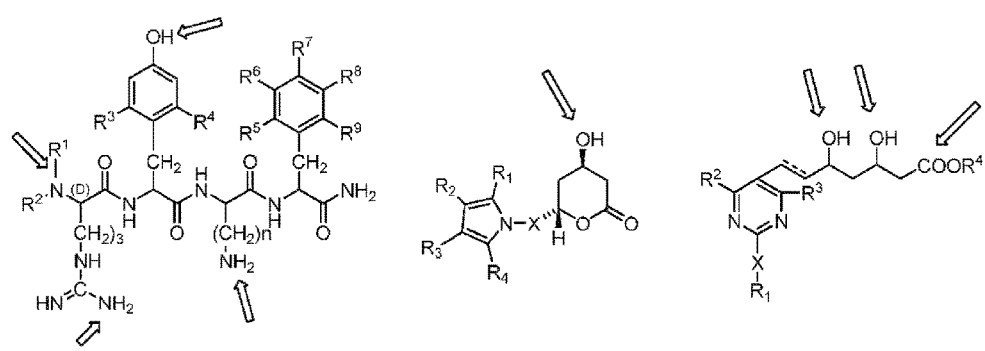
FIG. 9 is a diagram showing D-Arg-2'6'-Dmt-Lys-Phe-NH₂ and statin potential reactive linking sites for pro-drug formation (arrows).

Statins—As noted above, in one aspect, the present disclosure provides combination therapies for the treatment of atherosclerosis comprising administering an effective amount of peptide D-Arg-2'6'-Dmt-Lys-Phe-$NH_2$ or a pharmaceutically acceptable salt, such as acetate or trifluoroacetate salt in combination with one or more statins. In some embodiments the peptide D-Arg-2'6'-Dmt-Lys-Phe-$NH_2$ is chemically linked to the one or more statins. In some embodiments, the peptide is linked to the statin using a labile bond such that hydrolysis in vivo releases the two pharmaceutically active agents. A schematic diagram illustrating exemplary embodiments is shown in FIG. 7. In some embodiments, the linkage comprises an ester, a carbonate, a carbamate or other labile linkage. FIG. 8 shows illustrative embodiments where when X=O, a carbonate linked pro-drug is formed. One skilled in the art would understand that where X=NH, a carbamate linked pro-drug is formed. Potential reactive sites on the peptide D-Arg-2'6'-Dmt-Lys-Phe-$NH_2$ and statins are shown in FIG. 9.

Figure 10:
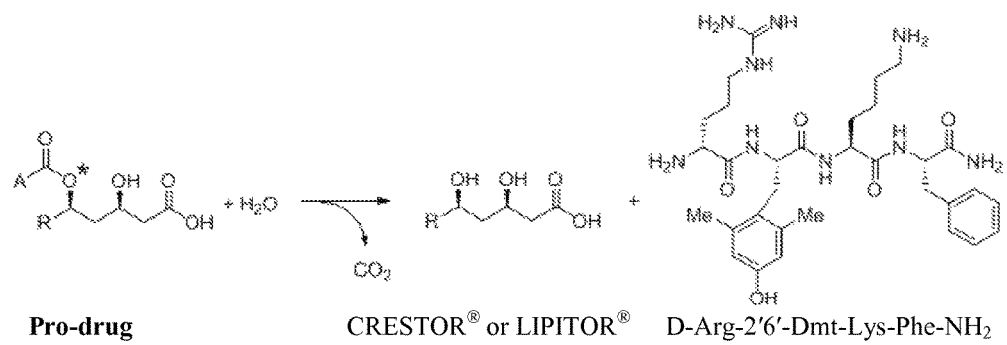
FIG. 10 shows illustrative pro-drugs in which the D-Arg-2'6'-Dmt-Lys-Phe-NH₂ peptide is linked to CRESTOR® or LIPITOR® using a carbonate linkage.
Figure 10:
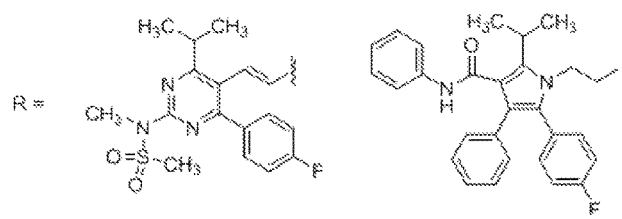
Figure 10:
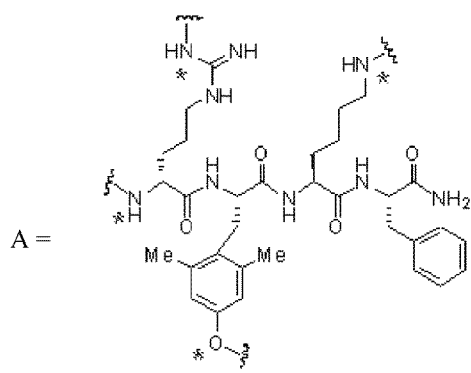
Figure 11:
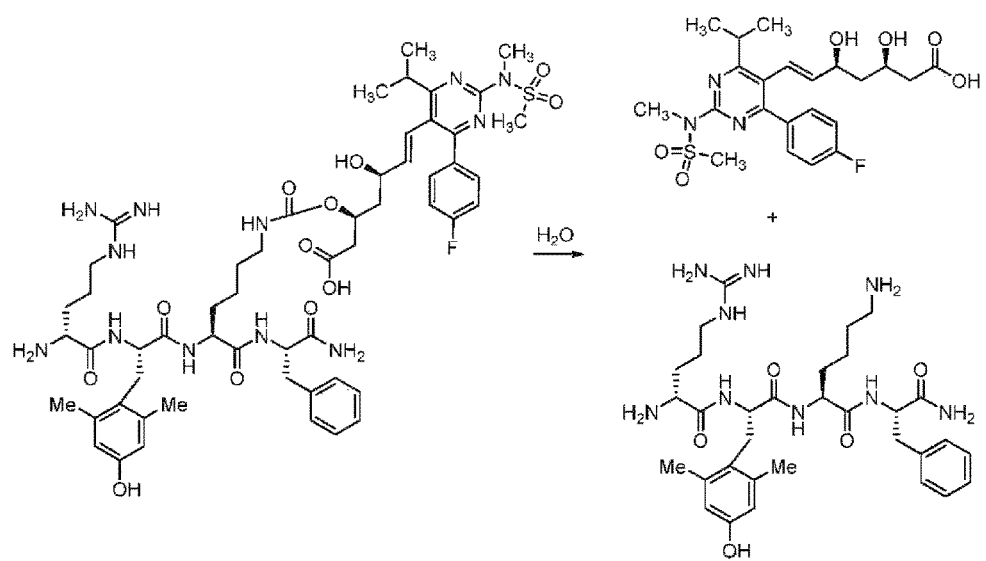
FIG. 11 shows illustrative pro-drugs in which the D-Arg-2'6'-Dmt-Lys-Phe-NH₂ peptide is linked to CRESTOR® using a carbamate linkage.

By way of example but not by way of limitation, FIG. 10 illustrates how D-Arg-2'6'-Dmt-Lys-Phe-$NH_2$ could be linked to either CRESTOR® or LIPITOR® using a carbonate linkage. By way of example but not by way of limitation, FIG. 11 illustrates how D-Arg-2'6'-Dmt-Lys-Phe-$NH_2$ could be linked to CRESTOR® using a carbamate linkage.

PCSK9—In some embodiments, the present disclosure provides combination therapies comprising administering an effective amount of peptide D-Arg-2'6'-Dmt-Lys-Phe-$NH_2$ or a pharmaceutically acceptable salt, such as acetate or trifluoroacetate salt in combination with one or more therapies targeting PCSK9. In some embodiments, the D-Arg-2'6'-Dmt-Lys-Phe-$NH_2$ peptide is conjugated to an anti-PCSK9 antibody to form a peptide-antibody conjugate. A variety of bifunctional protein coupling agents may be used. By way of example, but not by way of limitation, in some embodiments, the peptide-antibody conjugates are prepared using one or more of N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), or bis-active fluorine compounds (such as 1,5-difluoro-2,4-dinitrobenzene).

As noted above, in some embodiments, the peptide-antibody conjugate is generated using a cleavable linker to facilitate release of the peptide in vivo. In some embodiments, the cleavable linker is an acid-labile linker, peptidase-sensitive linker, photolabile linker, a dimethyl linker, or a disulfide-containing linker. In some embodiments, the linker is a labile linkage that is hydrolyzed in vivo to release the antibody and peptide. In some embodiments, the labile linkage comprises an ester linkage, a carbonate linkage, or a carbamate linkage.

Anti-Apo-B—In some embodiments, the peptide D-Arg-2'6'-Dmt-Lys-Phe-NH$_2$ is chemically linked to an anti-Apo-B agent (e.g., an anti-Apo-B RNA, e.g., an antisense RNA) using a labile linkage to form a pro-drug that upon hydrolysis in vivo releases the peptide and the anti-Apo-B agent as active agents. In some embodiments, the labile linkage comprises an ester linkage, a carbonate linkage, or a carbamate linkage. By way of illustration but not by way of limitation, FIG. 9 shows potential reactive sites on the peptide D-Arg-2'6'-Dmt-Lys-Phe-NH$_2$ at which an anti-Apo-B agent could be linked.

Additional Formulations—Combination Therapy

In some embodiments, the antihyperlipidemic agent and an aromatic cationic peptide of the present disclosure may be administered in the form of a pharmaceutical composition comprising at least one of the compounds disclosed herein together with a pharmaceutically acceptable carrier or diluent. Thus, in some embodiments, the compounds disclosed herein can be administered either individually or together in any conventional oral, parenteral or transdermal dosage form. In some embodiments, the antihyperlipidemic agent may be co-formulated in a fixed-dose combination with the aromatic cationic peptide. In some embodiments, the antihyperlipidemic agent and the aromatic cationic peptide are formulated in a capsule or pill for oral dosing in which the compounds are physically separated. In such a formulation, one or both of the antihyperlipidemic agent and the aromatic cationic peptide are in a solid, liquid, powder, or gel form. In some embodiments, the antihyperlipidemic agent and the aromatic cationic peptide are in a fixed-dose combination in which the two compounds are mixed together, for example in in a solid, liquid, powder, or gel form.

Dosage

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides and/or cardiovascular agents, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter.

In some embodiments, a therapeutically effective amount of an aromatic-cationic peptide may be defined as a concentration of peptide at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.0001 to about 0.5 mg/kg/h, suitably from about 0.001 to about 0.1 mg/kg/h. In one embodiment, the mid-dose is provided from about 0.01 to about 1.0 mg/kg/h, suitably from about 0.01 to about 0.5 mg/kg/h. In one embodiment, the high dose is provided from about 0.5 to about 10 mg/kg/h, suitably from about 0.5 to about 2 mg/kg/h. In an illustrative embodiment, the dose of cardiovascular agent is from about 1 to 100 mg/kg, suitably about 25 mg/kg.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In some embodiments, the mammal is a human.

EXAMPLES

The present invention is further illustrated by the following example, which should not be construed as limiting in any way.

Example 1

Effects of Aromatic-Cationic Peptides in Protecting Against Atherosclerosis in a Mouse Model The effects of aromatic-cationic peptides in protecting against atherosclerosis in a mouse model were investigated.

Apoprotein E deficient mice (Jackson Laboratories, 600 Main Street, Bar Harbor, Me.) were used in this study. The mice were male, 7-8 weeks of age, and between 18-20 g in weight. An initial total cholesterol measurement was made on 30 mice, and the mice were grouped into two groups of 15 to match the total cholesterol measurements. Both groups were fed a "western diet" (40 kcal % butterfat, 0.15% [wt/wt] cholesterol, Harlan Teklad diet TD-88137). Starting at t=0, the control group of 15 mice received vehicle only (phosphate buffered saline at pH 7.4), while the test group of 15 mice received aromatic-cationic peptide reconstituted in phosphate buffered saline. Body weights of the mice were recorded weekly, and mortality checks were performed daily.

The aromatic-cationic peptide D-Arg-2'6'-Dmt-Lys-Phe-NH$_2$ (sterile lyophilized powder, reconstituted in phosphate buffered saline) was tested. For the 12-week study, test mice received a single, daily dose of the peptide, subcutaneously at 1 mg/kg. Control mice received a single daily dose of vehicle.

Experimental Protocol/Data Collection. Blood was collected every four weeks (orbital plexis) under isoflurane anesthesia (3%) and blood lipids were determined. Plasma lipid analysis was conducted for both groups at t=0, 4, 6, 8, and 12 weeks. Plasma lipid analysis using an autoanalyzer included total cholesterol (TC), triglycerides (Trigs), phospholipids (PL), free cholesterol (FC), and cholesterol ester (CE, by calculation). Gel electrophoresis was used to measure levels of high-density lipoprotein cholesterol (HDL-C), low-density lipoprotein cholesterol (LDL-C), and very low-density lipoprotein cholesterol (VLDL-C).

Histopathology/Histomorphometery: Following the 12 week treatment, mice were euthanized within 48 hours after the last dose by CO$_2$ asphyxiation and the vascular tree was perfused with 5 mL of phosphate buffered saline (pH 7.4). The aorta and aortic sinus were removed for examination. Thoracic aorta were isolated, trimmed of fat, and fixed in formalin for 48-72 hours before analysis. For en face analysis, aortas were laid out and pinned on black matrix for photography, and stained with Sudan IV. Vessels were imaged for surface involvement using a Nikon computerized image analysis system and the percent of the aortic surface area covered by lipid was calculated. Two determinations were done for each image (Quan 1 and Quan 2), and the average was computed. The data were then computed by group and statistically analyzed. Following staining and morphometric analysis, total lipids were extracted from the aortas using the Bligh-Dyer method. WAKO Diagnostics kits (WAKO Diagnostics, Inc., 1600 Bellwood Road Richmond, Va. 23237-1326) were then used to evaluate total cholesterol, free cholesterol, and cholesterol ester. Cholesterol leves were quantitate nad expressed relative to protein levels. Values are expressed as µg lipid per mg protein (see e.g., FIG. 1).

For the aortic sinus, the heart and approximately 5 mm of the ascending aorta was cut from the remainder of the aorta. The apex of the heart was removed and remaining heart with the attached aortic segment was fixed and sectioned (in OCT medium and frozen in a dry ice—2 methylbutane bath). Serial 10 µm thick cryosections were made beginning with the ascending aorta and proceeding through the entire aortic sinus until the ventricular chamber was reached. The sections were stained with Oil Red O or Sudan IV and counter stained with Harris hematoxylin. Alternate sections were stained with hematoxylin and eosin. The sinus was imaged at 5 step levels in the region of interest, i.e., the aortic root, for a total distance of 300 µm and the lipid-staining areas and measured (total cross sectional area) using a Nikon computerized image analysis system. The data were then computed by group and statistically analyzed.

Results are shown in the tables below and in FIGS. 1-4. Table 7 shows the en face analysis of atherosclerotic lesions for each mouse in the study. Column 1: (sample ID #) represents each mouse, 1-15 are control animals (received vehicle alone), and 16-20 are test animals (received aromatic-cationic peptide); column 2: (Quan 1) shows a first determination of % of the aortic surface covered by lipid for each mouse in the study; column 3 (Quan 2) shows a second determination of % of the aortic surface covered by lipid for each mouse in the study; column 4: shows the average % of the surface of the aorta showing lesions for each mouse in the study; column 5 shows the average % of the surface of the aortas of control or test mice showing lesions; column 5 shows the standard error of the mean for each group (control or test animals). As shown in Table 7, treatment with the aromatic-cationic peptide reduces atherosclerotic lesions in the aorta. Aromatic-cationic peptides of the present disclosure are therefore useful in treating atherosclerosis and related signs, symptoms and complications of atherosclerosis.

TABLE 7

En Face Analysis of Atherosclerotic Lesions

| Sample ID# | Quan 1 | Quan 2 | Ave. % of Lesion | Ave | SEM |
|---|---|---|---|---|---|
| 1 | 5.810 | 6.517 | 6.164 | 7.189 | 0.990 |
| 2 | 4.501 | 5.089 | 4.795 | | |
| 3 | 2.637 | 3.567 | 3.102 | | |
| 4 | 3.416 | 3.719 | 3.568 | | |
| 5 | 18.228 | 17.115 | 17.672 | | |
| 6 | 2.951 | 3.919 | 3.435 | | |
| 7 | 11.164 | 10.464 | 10.814 | | |
| 8 | 4.492 | 4.538 | 4.515 | | |
| 9 | 6.002 | 6.080 | 6.041 | | |
| 10 | 6.303 | 5.610 | 5.957 | | |
| 11 | 10.293 | 12.311 | 11.302 | | |
| 12 | 8.044 | 7.019 | 7.532 | | |
| 13 | 9.162 | 8.497 | 8.830 | | |
| 14 | 8.610 | 7.629 | 8.120 | | |
| 15 | 6.000 | 5.981 | 5.991 | | |
| 16 | 2.562 | 2.667 | 2.615 | 5.328 | 1.027 |
| 17 | 0.914 | 0.870 | 0.892 | | |
| 18 | 8.769 | 9.284 | 9.027 | | |
| 19 | 2.832 | 3.205 | 3.019 | | |
| 20 | 7.137 | 6.881 | 7.009 | | |
| 21 | 5.198 | 4.468 | 4.833 | | |
| 22 | 2.128 | 1.863 | 1.996 | | |
| 23 | 1.388 | 1.021 | 1.205 | | |
| 24 | 10.000 | 9.895 | 9.948 | | |
| 25 | 2.990 | 2.536 | 2.763 | | |
| 26 | 7.091 | 6.536 | 6.814 | | |
| 27 | 4.700 | 4.768 | 4.734 | | |
| 28 | 0.775 | 0.892 | 0.834 | | |
| 29 | 11.589 | 10.888 | 11.239 | | |
| 30 | 13.857 | 12.122 | 12.990 | | |

Table 8 shows levels of total cholesterol (TC), free cholesterol (FC) and cholesterol ester (CE) in the thoracic aorta at 12 weeks for the 30 mice tested in the study. Mouse "sample" 1-15 are control mice (received vehicle only);

mouse "sample" 16-20 are test mice (received aromatic-cationic peptide). As shown in Table 8, treatment with aromatic-cationic peptides lowers the total cholesterol, free cholesterol and cholesterol esters in the thoracic aorta. Aromatic-cationic peptides of the present disclosure are therefore useful in treating atherosclerosis and related signs, symptoms and complications of atherosclerosis.

TABLE 8

Thoracic Aorta Lipids

|  | Sample # | TC µg/mg | FC µg/mg | CE µg/mg |
|---|---|---|---|---|
| Vehicle | 1 | 37.3 | 8.3 | 28.9 |
| Vehicle | 2 | 28.7 | 7.2 | 21.5 |
| Vehicle | 3 | 23.5 | 9.2 | 14.2 |
| Vehicle | 4 | 28.7 | 7.7 | 21.0 |
| Vehicle | 5 | 59.6 | 20.5 | 39.1 |
| Vehicle | 6 | 21.3 | 6.2 | 15.1 |
| Vehicle | 7 | 37.6 | 6.8 | 30.8 |
| Vehicle | 8 | 19.0 | 5.0 | 14.0 |
| Vehicle | 9 | 27.1 | 7.0 | 20.1 |
| Vehicle | 10 | 31.7 | 12.5 | 19.2 |
| Vehicle | 11 | 37.0 | 5.2 | 31.8 |
| Vehicle | 12 | 20.6 | 3.0 | 17.6 |
| Vehicle | 13 | 24.5 | 4.2 | 20.3 |
| Vehicle | 14 | 27.3 | 3.5 | 23.7 |
| Vehicle | 15 | 28.3 | 6.3 | 22.0 |
|  | AVE | 30.1 | 7.5 | 22.6 |
|  | SEM | 2.6 | 1.1 | 1.8 |
| Peptide | 16 | 21.4 | 7.6 | 13.8 |
| Peptide | 17 | 6.7 | 4.0 | 2.7 |
| Peptide | 18 | 35.4 | 5.1 | 30.3 |
| Peptide | 19 | 17.7 | 3.0 | 14.7 |
| Peptide | 20 | 38.8 | 8.1 | 30.7 |
| Peptide | 21 | 16.8 | 2.7 | 14.1 |
| Peptide | 22 | 8.1 | 3.5 | 4.6 |
| Peptide | 23 | 20.1 | 14.6 | 5.6 |
| Peptide | 24 | 35.1 | 6.6 | 28.5 |
| Peptide | 25 | 9.4 | 3.8 | 5.6 |
| Peptide | 26 | 24.9 | 3.6 | 21.3 |
| Peptide | 27 | 21.7 | 3.0 | 18.6 |
| Peptide | 28 | 7.9 | 3.3 | 4.6 |
| Peptide | 29 | 19.0 | 7.6 | 11.4 |
| Peptide | 30 | 22.5 | 9.5 | 13.0 |
|  | AVE | 20.4 | 5.7 | 14.6 |
|  | SEM | 2.6 | 0.9 | 2.5 |

Table 9 shows the total lesion area in the aortic root 300 µm across the aortic valve. Sample ID#1-15 are control mice (received vehicle only); Sample ID#16-20 are test mice (received aromatic-cationic peptide). As shown in Table 9, treatment with aromatic-cationic peptides reduces total lesion area. Aromatic-cationic peptides of the present disclosure are therefore useful in treating atherosclerosis and related signs, symptoms and complications of atherosclerosis.

TABLE 9

Total Lesion Area in Aortic Root 300 µm Across Aortic Valve

| Sample ID# | Area(mm$^2$) | Sample ID# | Area(mm$^2$) |
|---|---|---|---|
| 1 | 325.02 | 16 | 323.88 |
| 2 | 250.92 | 17 | 109.92 |
| 3 | 342.78 | 18 | 480.18 |
| 4 | 264.06 | 19 | 100.44 |
| 5 | 402.84 | 20 | 362.52 |
| 6 | 293.28 | 21 | 259.38 |
| 7 | 408.48 | 22 | 185.04 |
| 8 | 323.88 | 23 | 310.38 |
| 9 | 429.54 | 24 | 401.46 |
| 10 | 302.04 | 25 | 201.84 |
| 11 | 343.62 | 26 | 347.58 |
| 12 | 375.36 | 27 | 280.92 |
| 13 | 613.26 | 28 | 117.96 |
| 14 | 376.14 | 29 | 427.8 |
| 15 | 225.36 | 30 | 331.5 |
| AVE | 351.77 |  | 282.72 |
| SEM | 24.18 |  | 30.58 |

Table 10A-10D and FIGS. 4A-H show plasma lipid levels at t=0 weeks, 4 weeks, 8 weeks, and 12 weeks. For each of the tables, total cholesterol (TC), free cholesterol (FC), cholesterol ester (CE), triglycerides (Trigs) and phospholipid (PL) is shown for each of the 15 control (sample #1-15) and 15 test animals (sample #16-30). Also provided are average values (AVE), and standard error of the mean (SEM). As show in tables 10A-10D, and in FIGS. 4A-4H, at 4, 8 and 12 week time points, treatment with aromatic-cationic peptides reduces plasma total cholesterol, VLDL-C, LDL-C, free cholesterol, cholesterol ester, triglycerides and phospholipid levels. Aromatic-cationic peptides of the present disclosure are therefore useful in treating atherosclerosis and related signs, symptoms and complications of atherosclerosis.

TABLE 10A

Plasma Lipid Levels-Week 0

Spife (electrophoresis)Results

| Sample # | TC mg/dL | HDL-C mg/dL | VLDL-C mg/dL | LDL-C | FC | CE | Trigs | PL |
|---|---|---|---|---|---|---|---|---|
| 1 | 405 | 22 | 25 | 358 | 136 | 269 | 84 | 255 |
| 2 | 546 | 63 | 39 | 444 | 159 | 387 | 174 | 357 |
| 3 | 304 | 28 | 19 | 258 | 110 | 194 | 132 | 248 |
| 4 | 320 | 28 | 18 | 274 | 119 | 201 | 75 | 263 |
| 5 | 323 | 29 | 24 | 270 | 118 | 205 | 96 | 277 |
| 6 | 302 | 34 | 25 | 242 | 120 | 182 | 165 | 277 |
| 7 | 381 | 38 | 24 | 319 | 140 | 241 | 167 | 328 |
| 8 | 342 | 12 | 24 | 307 | 120 | 222 | 158 | 285 |
| 9 | 361 | 25 | 31 | 305 | 127 | 234 | 179 | 288 |
| 10 | 434 | 15 | 21 | 398 | 139 | 295 | 151 | 316 |
| 11 | 431 | 5 | 19 | 406 | 142 | 289 | 253 | 295 |
| 12 | 564 | 19 | 33 | 513 | 157 | 407 | 121 | 331 |
| 13 | 621 | 30 | 27 | 564 | 173 | 448 | 154 | 374 |
| 14 | 301 | 13 | 16 | 273 | 117 | 184 | 103 | 264 |
| 15 | 536 | 12 | 27 | 498 | 162 | 374 | 109 | 299 |
| AVE | 411 | 25 | 25 | 362 | 136 | 275 | 141 | 297 |
| SEM | 28 | 4 | 2 | 27 | 5 | 23 | 12 | 10 |
| 16 | 302 | 19 | 25 | 258 | 119 | 183 | 75 | 267 |
| 17 | 318 | 34 | 23 | 260 | 121 | 197 | 88 | 267 |
| 18 | 376 | 32 | 37 | 307 | 134 | 242 | 117 | 308 |
| 19 | 302 | 37 | 20 | 245 | 110 | 192 | 96 | 255 |
| 20 | 323 | 35 | 20 | 268 | 116 | 207 | 71 | 267 |
| 21 | 335 | 21 | 19 | 295 | 131 | 204 | 138 | 306 |
| 22 | 369 | 38 | 27 | 304 | 129 | 240 | 88 | 298 |
| 23 | 550 | 41 | 36 | 474 | 184 | 366 | 167 | 369 |
| 24 | 309 | 6 | 15 | 287 | 113 | 196 | 88 | 238 |
| 25 | 409 | 31 | 26 | 352 | 139 | 270 | 136 | 320 |
| 26 | 431 | 26 | 25 | 380 | 134 | 297 | 151 | 313 |
| 27 | 552 | 39 | 31 | 481 | 170 | 382 | 191 | 332 |
| 28 | 457 | 22 | 24 | 410 | 151 | 306 | 188 | 343 |
| 29 | 490 | 29 | 28 | 432 | 159 | 331 | 154 | 338 |
| 30 | 808 | 8 | 29 | 773 | 220 | 588 | 353 | 413 |
| AVE | 422 | 28 | 26 | 368 | 142 | 280 | 140 | 309 |
| SEM | 35 | 3 | 2 | 35 | 8 | 28 | 18 | 12 |

TABLE 10B

Plasma Lipid Levels-Week 4

*Spife (electrophoresis) Results*

| Sample # | TC | mg/dL HDL-C | mg/dL VLDL-C | mg/dL LDL-C | FC | CE | Trigs | PL |
|---|---|---|---|---|---|---|---|---|
| 1 | 1195 | 39 | 54 | 1101 | 456 | 739 | 82 | 634 |
| 2 | 1103 | 31 | 51 | 1022 | 394 | 709 | 54 | 558 |
| 3 | 1114 | 11 | 51 | 1052 | 424 | 690 | 44 | 540 |
| 4 | 876 | 18 | 37 | 822 | 328 | 548 | 59 | 436 |
| 5 | 1124 | 11 | 58 | 1058 | 444 | 680 | 18 | 480 |
| 6 | 913 | 23 | 27 | 863 | 332 | 581 | 62 | 456 |
| 7 | 1052 | 25 | 48 | 978 | 382 | 670 | 54 | 528 |
| 8 | 908 | 15 | 31 | 862 | 352 | 556 | 72 | 460 |
| 9 | 948 | 16 | 38 | 894 | 372 | 576 | 72 | 470 |
| 10 | 850 | 20 | 37 | 794 | 338 | 512 | 64 | 420 |
| 11 | 1245 | 32 | 34 | 1181 | 502 | 743 | 75 | 590 |
| 12 | 1274 | 42 | 32 | 1200 | 582 | 692 | 128 | 690 |
| 13 | 1267 | 33 | 22 | 1212 | 524 | 743 | 98 | 658 |
| 14 | 1116 | 32 | 30 | 1054 | 406 | 710 | 57 | 540 |
| 15 | 1177 | 32 | 29 | 1115 | 510 | 667 | 57 | 568 |
| AVE | 1078 | 25 | 39 | 1014 | 423 | 654 | 66 | 535 |
| SEM | 38 | 3 | 3 | 36 | 20 | 20 | 6 | 21 |
| 16 | 799 | 18 | 35 | 745 | 308 | 491 | 18 | 422 |
| 17 | 924 | 20 | 37 | 866 | 344 | 580 | 39 | 482 |
| 18 | 976 | 20 | 37 | 918 | 354 | 622 | 28 | 452 |
| 19 | 1139 | 0 | 19 | 1120 | 408 | 731 | 85 | 560 |
| 20 | 1038 | 13 | 44 | 982 | 412 | 626 | 59 | 526 |
| 21 | 673 | 7 | 18 | 648 | 256 | 417 | 18 | 320 |
| 22 | 940 | 23 | 23 | 893 | 366 | 574 | 46 | 506 |
| 23 | 1046 | 32 | 39 | 975 | 386 | 660 | 108 | 556 |
| 24 | 835 | 20 | 44 | 770 | 320 | 515 | 59 | 446 |
| 25 | 822 | 15 | 41 | 766 | 286 | 536 | 33 | 416 |
| 26 | 1026 | 32 | 28 | 966 | 396 | 630 | 44 | 516 |
| 27 | 1223 | 45 | 31 | 1147 | 462 | 761 | 67 | 580 |
| 28 | 935 | 32 | 30 | 874 | 354 | 581 | 44 | 510 |
| 29 | 1248 | 44 | 32 | 1171 | 516 | 732 | 80 | 666 |
| 30 | 1337 | 49 | 35 | 1254 | 636 | 701 | 144 | 750 |
| AVE | 997 | 25 | 33 | 940 | 387 | 610 | 58 | 514 |
| SEM | 47 | 4 | 2 | 45 | 25 | 25 | 9 | 27 |

TABLE 10C

Plasma Lipid Levels-Week 8

*Spife (electrophoresis) Results*

| Sample # | TC | mg/dL HDL-C | mg/dL VLDL-C | mg/dL LDL-C | FC | CE | Trigs | PL |
|---|---|---|---|---|---|---|---|---|
| 1 | 1590 | 26 | 76 | 1488 | 418 | 1172 | 79 | 548 |
| 2 | 1342 | 10 | 107 | 1225 | 352 | 990 | 58 | 518 |
| 3 | 1270 | 4 | 66 | 1201 | 346 | 924 | 39 | 482 |
| 4 | 1611 | 40 | 82 | 1489 | 394 | 1217 | 60 | 526 |
| 5 | 1610 | 16 | 107 | 1488 | 420 | 1190 | 79 | 536 |
| 6 | 902 | 19 | 51 | 831 | 278 | 624 | 53 | 410 |
| 7 | 1484 | 28 | 54 | 1402 | 408 | 1076 | 89 | 564 |
| 8 | 986 | 23 | 75 | 887 | 288 | 698 | 58 | 380 |
| 9 | 1491 | 24 | 70 | 1397 | 394 | 1097 | 65 | 554 |
| 10 | 1568 | 23 | 86 | 1459 | 388 | 1180 | 63 | 534 |
| 11 | 1667 | 30 | 149 | 1488 | 470 | 1197 | 113 | 594 |
| 12 | 1842 | 86 | 143 | 1613 | 574 | 1268 | 209 | 738 |
| 13 | 1695 | 62 | 137 | 1496 | 448 | 1247 | 142 | 534 |
| 14 | 1719 | 22 | 106 | 1591 | 454 | 1265 | 96 | 570 |
| 15 | 765 | 18 | 39 | 708 | 250 | 515 | 41 | 396 |
| AVE | 1436 | 29 | 90 | 1318 | 392 | 1044 | 83 | 526 |
| SEM | 83 | 5 | 9 | 74 | 21 | 64 | 11 | 23 |
| 16 | 1262 | 42 | 101 | 1119 | 322 | 940 | 34 | 416 |
| 17 | 1004 | 34 | 73 | 897 | 294 | 710 | 31 | 456 |
| 18 | 1505 | 27 | 86 | 1392 | 386 | 1119 | 34 | 474 |
| 19 | 1183 | 33 | 79 | 1071 | 318 | 865 | 51 | 448 |
| 20 | 1545 | 19 | 112 | 1415 | 392 | 1153 | 48 | 516 |
| 21 | 943 | 8 | 34 | 901 | 290 | 653 | 31 | 424 |
| 22 | 1008 | 45 | 88 | 875 | 294 | 714 | 51 | 480 |
| 23 | 1473 | 16 | 79 | 1378 | 388 | 1085 | 53 | 488 |
| 24 | 1023 | 32 | 69 | 922 | 308 | 715 | 43 | 436 |

TABLE 10C-continued

Plasma Lipid Levels-Week 8

*Spife (electrophoresis) Results*

| Sample # | TC | mg/dL HDL-C | mg/dL VLDL-C | mg/dL LDL-C | FC | CE | Trigs | PL |
|---|---|---|---|---|---|---|---|---|
| 25 | 956 | 41 | 59 | 856 | 286 | 670 | 75 | 440 |
| 26 | 1435 | 25 | 93 | 1317 | 362 | 1073 | 63 | 556 |
| 27 | 1414 | 19 | 74 | 1320 | 366 | 1048 | 39 | 516 |
| 28 | 1147 | 41 | 80 | 1025 | 308 | 839 | 34 | 470 |
| 29 | 1534 | 43 | 109 | 1382 | 404 | 1130 | 67 | 540 |
| 30 | 1797 | 57 | 119 | 1621 | 530 | 1267 | 195 | 728 |
| AVE | 1282 | 32 | 84 | 1166 | 350 | 932 | 57 | 493 |
| SEM | 69 | 3 | 6 | 64 | 17 | 53 | 10 | 20 |

TABLE 10D

Plasma Lipid Levles-Week 12

*Spife (electrophoresis) Results*

| Sample # | TC | mg/dL HD L-C | mg/dL VLDL-C | mg/dL LDL-C | FC | CE | Trigs | PL |
|---|---|---|---|---|---|---|---|---|
| 1 | 1115 | 39 | 36 | 1041 | 351 | 764 | 42 | 444 |
| 2 | 637 | 15 | 35 | 587 | 225 | 412 | 25 | 336 |
| 3 | 803 | 23 | 24 | 756 | 269 | 533 | 25 | 381 |
| 4 | 1243 | 48 | 105 | 1090 | 380 | 863 | 31 | 477 |
| 5 | 1335 | 9 | 69 | 1257 | 429 | 907 | 11 | 499 |
| 6 | 874 | 28 | 36 | 811 | 307 | 567 | 31 | 427 |
| 7 | 1077 | 35 | 43 | 998 | 346 | 731 | 20 | 445 |
| 8 | 827 | 23 | 44 | 759 | 277 | 550 | 20 | 379 |
| 9 | 1205 | 27 | 43 | 1135 | 376 | 829 | 24 | 586 |
| 10 | 910 | 36 | 44 | 830 | 306 | 604 | 16 | 417 |
| 11 | 1220 | 50 | 62 | 1108 | 371 | 848 | 93 | 497 |
| 12 | 1754 | 56 | 59 | 1640 | 543 | 1211 | 60 | 700 |
| 13 | 1710 | 17 | 83 | 1609 | 558 | 1152 | 97 | 689 |
| 14 | 1085 | 38 | 76 | 972 | 359 | 725 | 51 | 422 |
| 15 | 750 | 12 | 31 | 707 | 269 | 482 | 60 | 396 |
| AVE | 1103 | 30 | 53 | 1020 | 358 | 745 | 40 | 473 |
| SEM | 84 | 4 | 6 | 79 | 24 | 60 | 7 | 28 |
| 16 | 898 | 38 | 39 | 821 | 291 | 607 | 27 | 366 |
| 17 | 540 | 20 | 35 | 485 | 205 | 335 | 49 | 318 |
| 18 | 884 | 10 | 21 | 854 | 287 | 597 | 10 | 320 |
| 19 | 937 | 41 | 43 | 852 | 296 | 640 | 37 | 432 |
| 20 | 1420 | 21 | 71 | 1328 | 418 | 1002 | 18 | 491 |
| 21 | 719 | 5 | 21 | 693 | 242 | 477 | 39 | 321 |
| 22 | 674 | 31 | 32 | 611 | 229 | 445 | 39 | 363 |
| 23 | 745 | 20 | 33 | 692 | 269 | 476 | 37 | 394 |
| 24 | 990 | 2 | 26 | 962 | 315 | 675 | 13 | 374 |
| 25 | 999 | 40 | 63 | 896 | 312 | 687 | 25 | 423 |
| 26 | 1379 | 28 | 76 | 1275 | 419 | 960 | 74 | 536 |
| 27 | 1255 | 1 | 36 | 1218 | 386 | 869 | 89 | 521 |
| 28 | 558 | 23 | 30 | 505 | 219 | 339 | 97 | 340 |
| 29 | 1317 | 31 | 83 | 1203 | 413 | 904 | 112 | 575 |
| 30 | 1736 | 2 | 46 | 1688 | 535 | 1201 | 158 | 761 |
| AVE | 1003 | 21 | 44 | 939 | 322 | 681 | 55 | 434 |
| SEM | 90 | 4 | 5 | 88 | 24 | 66 | 11 | 31 |

Figure 2:
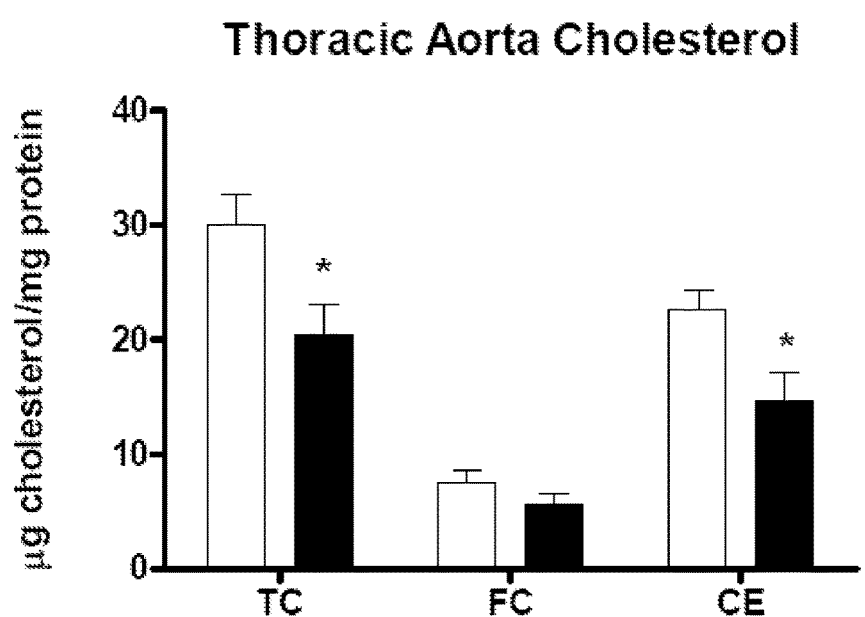
FIG. 2 is a graph showing the thoracic aorta cholesterol (m/mg protein) in control mice (vehicle only—white bars) and test mice (aromatic-cationic peptide D-Arg-2'6'-Dmt-Lys-Phe-NH$_2$—dark bars) after 12 weeks of vehicle or peptide administration. TC=total cholesterol; FC=free cholesterol; CE=cholesterol ester.
Figure 3:
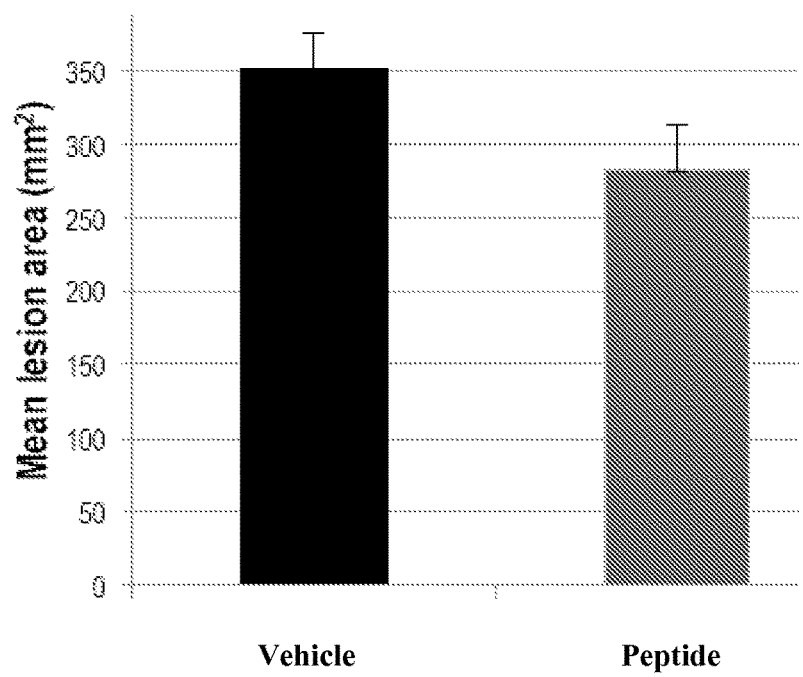
FIG. 3 is a graph showing mean leasion area (mm²) in control mice (vehicle only) and test mice (aromatic-cationic peptide D-Arg-2'6'-Dmt-Lys-Phe-NH₂) after 12 weeks.
Figure 4:
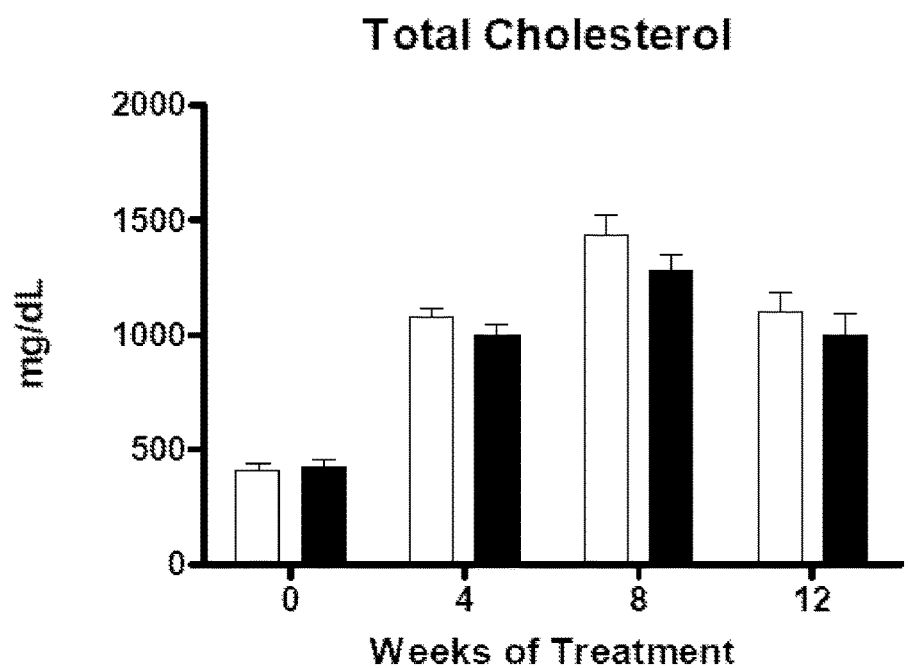
FIG. 4A-H show levels of (A) total cholesterol; (B) free cholesterol; (C) cholesterol ester; (D) HDL-C; (E) VLDL-C; (F) LDL-C; (G) triglycerides; and (H) phospholipids after 0, 4, 8 and 12 weeks of treatment with vehicle or peptide administration. Light bars in each panel represent data from control mice (vehicle only); dark bars represent data from the test mice (aromatic-cationic peptide D-Arg-2'6'-Dmt-Lys-Phe-NH₂).
Figure 4:
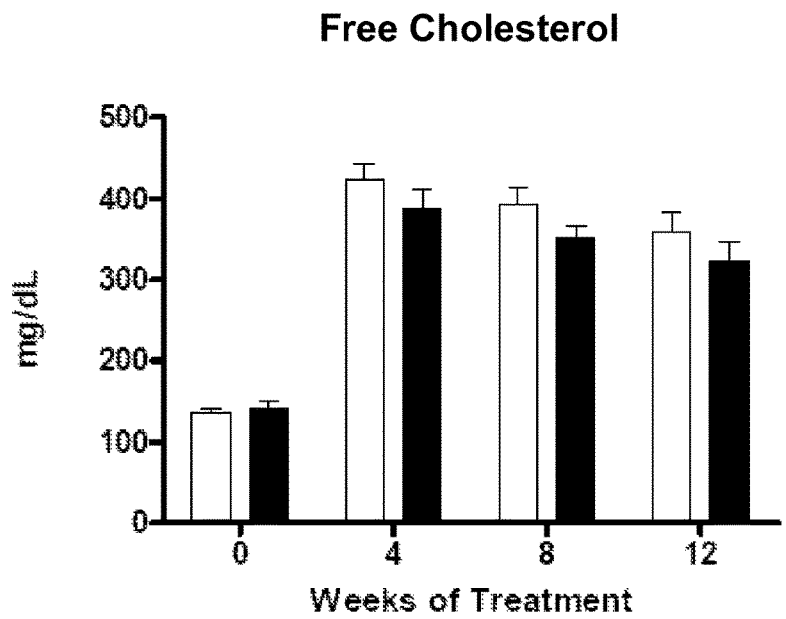

Results are further shown in FIGS. 1-3. FIG. 1A shows that at 12 weeks, the % lesion area is lower in the treated (dark bar) versus untreated (white bars) group. Thus there is a decrease in plaque present in the thoracic aorta of treated versus untreated subjects. FIG. 1B is a photograph of lesions on the vehicle only aorta versus the treated aorta. As shown in the bar graph in FIG. 2, the level of thoracic aorta plaque cholesterol content (TC=total cholesterol; FC=free cholesterol and CE=cholesterol ester) is lower in the treated (dark bars) versus untreated (vehicle, white bars) group at 12 weeks. FIG. 3 shows that, at 12 weeks, mean lesion area is lower in the treated group versus the untreated (vehicle) group. Accordingly, the aromatic-cationic peptides of the present disclosure are useful for decreasing the amount of atherosclerotic plaque in both the aorta and aortic root, and for decreasing the plaque cholesterol content. Thus, the aromatic-cationic peptides of the present disclosure are useful for treating or preventing atherosclerosis and related signs, symptoms and complications of atherosclerosis.

Example 2

Effects of Aromatic-Cationic Peptides in Conjunction with an Antihyperlipidemic Agent (e.g., Statins) to Protect Against Atherosclerosis and Lower Cholesterol Levels in a Mouse Model The effects of aromatic-cationic peptides in protecting against atherosclerosis, in conjunction with one or more antihyperlipidemic agents, in this example, statins, in a mouse model are investigated as follows.

Mice are treated as described in Example 1. That is, Apoprotein E deficient mice as described in Example 1 are used in the study. An initial total cholesterol measurement is made on the mice, and the mice are grouped into groups of 15 to match the total cholesterol measurements. The groups are fed a "western diet" (40 kcal % butterfat, 0.15% [wt/wt] cholesterol). Starting at t=0, the control group of 15 mice receives vehicle only, while the test groups of 15 mice receive aromatic-cationic peptide and one or more statins. Body weights of the mice are recorded weekly, and mortality checks are performed daily.

The aromatic-cationic peptide D-Arg-2'6'-Dmt-Lys-Phe-NH$_2$ (sterile lyophilized powder) is tested. Each group of test mice receives a single, daily dose of the peptide, subcutaneously at 1, 3, 5 or 10 mg/kg, and also receives, simultaneously atorvastatin, fluvastatin, lovastatin, pravastatin or rosuvastatin at 0.1, 0.5, 0.75 or 1 mg/kg. Control mice receive vehicle only. The injections continue for 12 weeks, at which time the mice are sacrificed and analyzed as described in Example 1.

Plasma lipid analysis using an autoanalyzer includes an evaluation of total cholesterol (TC), triglycerides (Trigs), phospholipids (PL), free cholesterol (FC), and cholesterol ester (CE, by calculation). Gel electrophoresis is used to measure levels of high-density lipoprotein cholesterol (HDL-C), low-density lipoprotein cholesterol (LDL-C), and very low-density lipoprotein cholesterol (VLDL-C). Histopathology/histomorphometery is performed as described above in Example 1.

Results: It is anticipated that mice receiving both the peptide and the statin will show decreased levels of total cholesterol, free cholesterol, triglyceride, phospholipid, cholesterol ester, LDL-C and VLDL-C as well as a decrease in the lesions as compared to subjects receiving vehicle only. It is also anticipated that in some instances, subjects receiving the combination treatment (aromatic-cationic peptide plus statin) will exhibit a synergy between the two drugs, such that a lower dose of peptide, the statin or both will achieve desired results, e.g., lowered levels of total cholesterol, free cholesterol, triglyceride, phospholipid, cholesterol ester, LDL-C and VLDL-C and/or lesions.

Accordingly, it is anticipated that the results will further demonstrate that the aromatic-cationic peptides of the present disclosure, alone or in combination with one or more statins, will be useful for treating atherosclerosis, and signs, symptoms or complications of atherosclerosis, including but not limited to increased total cholesterol, free cholesterol, triglyceride, phospholipid, cholesterol ester, LDL-C and VLDL-C and increased atherosclerotic lesions.

Example 3

Aromatic-cationic Peptides Increase Coenzyme Q10 Levels

Fibroblasts were treated with an aromatic-cationic peptide of the present disclosure, and levels of coenzyme Q10 were evaluated.

Human skin fibroblasts from normal subjects were incubated under standard tissue culture medium containing high glucose levels to support anaerobic conditions. At approximately 90% confluence, cells were incubated in the presence of 10 nM D-Arg-2'6'-Dmt-Lys-Phe-NH$_2$ for a period of either one day (24 h) or five days as shown in Table 11 below. The culture medium was not changed during the incubation period. Cells were harvested and the cellular level of CoQ was determined using methods known in the art. Data represents the average n=3-6.

TABLE 11

Treatment of fibroblasts with aromatic-cationic peptide

| Cells | Medium | Peptide Amount | Time of Peptide Treatment |
| --- | --- | --- | --- |
| fibroblast cells | DMEM | 0 | 0 |
| fibroblast cells | DMEM | 10 nM | 16-24 hours |
| fibroblast cells | DMEM | 10 nM | 5 days |

Results are shown in FIG. 5. As shown in FIG. 5, exposure to the aromatic-cationic peptides of the present disclosure increased coenzyme Q10 levels in fibroblast cells. Accordingly, the aromatic-cationic peptides of the present disclosure are useful for increasing coenzyme Q10 levels in subjects in need thereof. For example, the aromatic-cationic peptides of the present disclosure are useful for increasing coenzyme Q10 levels in subjects taking one or more statin drugs and/or in subjects suffering from a disease or conditions characterized by, or caused by low (e.g., below normal or control levels) coenzyme Q10 levels. The aromatic-cationic peptides of the present disclosure are useful to treat, prevent or ameliorate the signs and/or symptoms of diseases or conditions characterized by low (e.g., below normal or control levels) coenzyme Q10 levels.

\* \* \*

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for delaying onset, ameliorating or eliminating statin side effects in a subject in need thereof, the method comprising administering an effective amount of a peptide D-Arg-2'6'-Dmt-Lys-Phe-NH$_2$ or a pharmaceutically acceptable salt thereof, wherein the peptide is chemically linked to the statin, wherein the statin side effect comprises one or more of rhabdomyolysis, kidney failure, diabetes, memory loss, and decreased coenzyme Q10 levels.

2. The method of claim 1, wherein the statin is selected from the group consisting of: atorvastatin, simvastatin, pravastatin, fluvastatin, lovastatin, pitavastatin, rosuvastatin, niacin extended-release/lovastatin, lovastatin extended-release, amlodipine, atorvastatin, rosuvastatin, sitagliptin/simvastatin, fluvastatin, fluvastatin extended-release, atorvastatin, pitavastatin, lovastatin, pravastatin, niacin extended-release/simvastatin, ezetimibe/simvastatin, and simvastatin.

3. The method of claim 1, wherein the pharmaceutically acceptable salt comprises acetate salt or trifluoroacetate salt.

4. The method of claim 1, wherein the peptide and the statin are linked using a labile linkage that is hydrolyzed in vivo to release the peptide and the statin.

5. The method of claim 1, wherein the statin comprises atorvastatin or rosuvastatin.

6. The method of claim 4, wherein the labile linkage comprises an ester linkage, a carbonate linkage, or a carbamate linkage.

* * * * *